(12) United States Patent
Werker et al.

(10) Patent No.: US 8,748,138 B2
(45) Date of Patent: Jun. 10, 2014

(54) METHOD FOR ACCUMULATION OF POLYHYDROXYALKANOATES IN BIOMASS WITH ON-LINE MONITORING FOR FEED RATE CONTROL AND PROCESS TERMINATION

(75) Inventors: Alan Gideon Werker, Lomma (SE); Simon Olof Harald Bengtsson, Lund (SE); Carl Anton Börje Karlsson, Lund (SE)

(73) Assignee: Veolia Water Solutions & Technologies Support, Saint-Maurice (FR)

( * ) Notice: Subject to any disclaimer, the term of this patent is extended or adjusted under 35 U.S.C. 154(b) by 0 days.

(21) Appl. No.: 13/514,660

(22) PCT Filed: Dec. 10, 2010

(86) PCT No.: PCT/IB2010/055745
§ 371 (c)(1),
(2), (4) Date: Oct. 16, 2012

(87) PCT Pub. No.: WO2011/070544
PCT Pub. Date: Jun. 16, 2011

(65) Prior Publication Data
US 2013/0029388 A1    Jan. 31, 2013

Related U.S. Application Data

(60) Provisional application No. 61/285,210, filed on Dec. 10, 2009.

(51) Int. Cl.
*C12P 7/62* (2006.01)
*C02F 3/30* (2006.01)
*C12P 7/40* (2006.01)

(52) U.S. Cl.
CPC .. *C02F 3/30* (2013.01); *C12P 7/625* (2013.01)
USPC ............. 435/135; 435/41; 435/132; 435/136; 435/170; 435/262; 435/262.5

(58) Field of Classification Search
CPC .................................... C02F 3/30; C12P 7/625
See application file for complete search history.

(56) References Cited

U.S. PATENT DOCUMENTS

| | | | |
|---|---|---|---|
| 6,987,011 B1 * | 1/2006 | Reid et al. | 435/135 |
| 6,991,931 B2 * | 1/2006 | Dragotta et al. | 435/262 |
| 7,820,047 B2 * | 10/2010 | Yerushalmi et al. | 210/615 |
| 2008/0110828 A1 * | 5/2008 | Yerushalmi et al. | 210/620 |

FOREIGN PATENT DOCUMENTS

| | | | |
|---|---|---|---|
| EP | 1400569 A2 | 3/2004 | |
| WO | 0136652 A1 | 5/2001 | |
| WO | 2010092472 A2 | 8/2010 | |

OTHER PUBLICATIONS

Pederson, Erik N; et al; "Bacterial Synthesis of PHA Block Copolymers" Biomacromolecules, 7, 1904-1911, 2006.*
Chua, Adeline SM; et al "Production of polyhydroxyalkanoates by activated sludge treating municipal wastewater: effect of pH, sludge retention time, and acetate concentration in influent" Water Research, 37, 3602-3611, 2003.*
Salehizadeh, H; Van Loosdrect, MCM; "Production of polyhydroxyalkanoates by mixed culture: recent trends and biotechnological importance" Biotechnology Advances, 22, 261-279, 2004.*
Dircks, Klaus; et al; "Yield determination by respirometry—The possible influence of storage under aerobic conditions in activated sludge" Water SA, 25, 69-74, 1999.*
Kasemsap, Charuvan; Wantawin, Chalermraj; "Batch production of polyhydroxyalkanoate by low-polyphosphate-content activated sludge at varying pH" Bioresource Technology, 98, 1020-1027.*
Dionisi, Davide; et al; "Biodegradable Polymers From Organic Acids by Using Activated Sludge Enriched by Aerobic Periodic Feeding" Biotechnology and Bioengineering, 85, 569-579, 2004.*
Dionisi, Davide; et al; "Storage of biodegradable polymers by an enriched microbial community in a sequencing batch reactor operated at high organic load rate" Journal of Chemical Technology and Biotechnology, 80, 1306-1318, 2005.*
Jeon, Che Ok; et al; "Enhanced Biological Phosphorus Removal in an Anaerobic—Aerobic Sequencing Batch Reactor: Effect of pH" Water Environment Research, 73, 301-306, 2001.*
Guocheng, Du, "Fed fermentation production of biodegradable polymers", Biotechnology, Apr. 30, 1996, pp. 5-10.
Wei, Li, et al., "Polyhydroxyalkanoate (PHA) Synthesis by Activated Sludge Microbes Using Acetic Acid as Carbon Source", Environmental Science, Aug. 31, 2009, pp. 2366-2370, vol. 30, No. 8.
CN Search Report issued Jul. 24, 2013 in re CN Application No. 201080063564.1 filed Aug. 10, 2012.
Coats E., et al., "Toward Polyhydroxyalkanoate Production Concurrent with Municipal Wastewater Treatment in a Sequencing Batch Reactor System", Journal of Environmental Engineering, Jan. 1, 2011, pp. 46-54, vol. 137, Issue 1.

(Continued)

*Primary Examiner* — Blaine Lankford
*Assistant Examiner* — David Berke-Schlessel
(74) *Attorney, Agent, or Firm* — Coats and Bennett PLLC

(57) ABSTRACT

A method or process for producing polyhydroxyalkanoates (PHAs) in biomass. The process entails feeding an organic carbon containing substrate to biomass enriched in PHA accumulating bacteria. Particularly the process entails intermittently supplying the substrate to the biomass at least three separate times over a selected period. The object of the process is to produce PHA having a relatively high molecular weight, at least 400,000 g/mole. By controlling the frequency at which the substrate is supplied to the biomass and by feeding a sufficient amount of the substrate to the biomass, the method or process produces the PHA having the relatively high molecular weight.

18 Claims, 11 Drawing Sheets

(56) References Cited

OTHER PUBLICATIONS

Albuguerque, M.G.E., et al. "Mixed culture polyhydroxyalkanoate (PHA) production from volatile fatty acid (VFA)—rich streams: Effect of substrate composition and feeding regime on PHA productivity, composition and properties", Journal of Biotechnology, Jan. 10, 2011, pp. 66-76, vol. 151, issue 1, Elsevier NLD.

Morgan-Sagastume F., et al., "Production of polyhydroxyalkanoates in open, mixed cultures from a waste sludge stream containing high levels of soluble organics, nitrogen and phosphorus", Water Research, Oct. 1, 2010, pp. 5196-5211, vol. 44, issue 18, Elsevier Ltd.

Bengtsson, S., et al., "The utilization of glycogen accumulating organisms for mixed culture production of polyhydroxyalkanoates", Biotechnology and Bioengineering, Nov. 1, 2009, pp. 698-708, vol. 104, Issue 4, Wiley Periodicals, Inc.

Albuguerque, M.G. E., et al., "Strategies for the development of a side stream process for polyhydroxyalkanoate (PHA) production from sugar cane molasses", Journal of Biotechnology, Jul. 15, 2007, pp. 411-421, vol. 130, issue 4, Elsevier B.V.

Johnson, K., et al., "Model-based data evaluation of polyhydroxybutyrate producing mixed microbial cultures in aerobic sequencing batch and fed-batch reactors", Biotechnology and Bioengineering, Sep. 1, 2009, pp. 50-67, vol. 104, issue 1, Wiley Periodicals, Inc.

Reis, M. A. M., et al., "Production of polyhydroxyalkanoates by mixed microbial cultures", Bioprocess and Biosystems Engineering, Jul. 1, 2003, pp. 377-385, vol. 25, issue 6, Springer-Verlag.

Westeberg, K., "Using the Dissolved Oxygen Signal for Automatic Control in Fed-Batch Production of PHA by a Mixed Culture", [retrieved on Oct. 11, 2013], retrieved from Internet: http://www.chemeng.lth.se/exjobb/E470.pdf.

Nyman, A-K., "Influence of operating conditions on fedbatch production of polyhydroxyalkanoates in a mixed culture", Master Thesis, 2010, [retrieved on Oct. 11, 2013], retrieved from internet: www.chemeng.lth.se/exjobb/E508.pdf.

Akesson, M., et al., "A pulse technique for control of fed-batch fermentations", Proceedings of the 1997 IEEE International Conference on Control Applications, Oct. 5, 1997, pp. 139-144, IEEE, US.

Ganduri, V.S.R.K., et al., "Mixing control as a device to increase PHB production in batch fermentations with co-cultures of *Lactobacillus delbrueckii* and *Ralstonia eutropha*", Process Biochemistry, Jan. 1, 2005, vol. 40, issue 1, pp. 257-264.

Taga, N., et al., "Effects of rheological change by addition of carboxymethylcellulose in culture media of an air-lift fermentor on poly-D-3-hydroxybutyric acid productivity in autotrophic culture of hydrogen-oxidizing bacterium, *Alcaligenes eutrophus*", Biotechnology and Bioengineering, Mar. 5, 1997, pp. 529-533, vol. 53, issue 5, John Wiley & Sons, Inc.

Patel, M., et al., "Physico-chemical properties of polyhydroxyalkanoate produced by mixed-culture nitrogen-fixing bacteria", Applied Microbiology and Biotechnology, Mar. 1, 2009, pp. 545-555, vol. 82, Issue 3, Springer-Verlag.

\* cited by examiner

METHOD FOR ACCUMULATION OF POLYHYDROXYALKANOATES IN BIOMASS WITH ON-LINE MONITORING FOR FEED RATE CONTROL AND PROCESS TERMINATION

CROSS-REFERENCE TO RELATED APPLICATION

This application is a U.S. National Stage application of PCT application No. PCT/IB2010/055745, with an international filing date of Jun. 16, 2011. Applicant claims priority based on U.S. Provisional Patent Application No. 61/285,210 filed Dec. 10, 2009. The subject matter of these applications are incorporated herein.

TECHNICAL FIELD

This invention relates to the accumulation of polyhydroxyalkanoates (PHAs) in biomass in conjunction with biological organic waste treatment. The invention concerns the art of combining wastewater rich in readily biodegradable chemical oxygen demand (RBCOD) with biomass enriched in PHA-accumulating bacteria (PAB), and monitoring the process.

BACKGROUND OF THE INVENTION

Polyhydroxyalkanoates (PHAs) are biopolymers that can be compounded into engineering plastics or further converted into other platform chemicals with the side benefit of being entirely biodegradable. PHA accumulation can be used as part of an overall biorefinery concept for a wastewater treatment process comprising:
  I. acidogenic fermentation of organic material in the wastewater influent to produce volatile fatty acids (VFAs);
  II. removal of organic matter from the wastewater and production of a biomass, from the wastewater or other suitable source, with potential for significant accumulation of PHAs;
  III. production and accumulation of PHAs in the produced biomass from RBCOD-rich feed derived from the wastewater or other on- or off-site influent sources; and
  IV. recovery and purification of the PHAs.

The present invention may be useful for solving a number of problems associated with process quality objectives of PHA accumulation in PAB-rich biomass and wastewater treatment as explained further below.

SUMMARY OF THE INVENTION

The present invention provides methods of producing and accumulating PHAs in a PAB-rich biomass from RCBOD.

In one aspect, the invention provides a method for producing polyhydroyxalkanoates (PHAs) in biomass, comprising feeding an organic carbon-containing substrate to the biomass by intermittently supplying the substrate to the biomass over a period of time and controlling the frequency of the intermittent supply and amount of the intermittent supply of the substrate to the biomass such that the average molecular weight of the PHAs produced is at least 400,000 g/mole.

In another aspect, the invention provides a method of promoting the accumulation of PHAs in biomass, comprising feeding an organic carbon-containing substrate to the biomass by mixing substrate containing readily biodegradable chemical oxygen demand (RBCOD) with the biomass to form a biomass-substrate mixture, controlling the concentration of the RBCOD in the biomass-substrate mixture such that during PHA accumulation the concentration of RBCOD in the biomass-substrate mixture is generally maintained between 1,000 mg-COD/L and 10 mg-COD/L, and wherein the method of feeding RBCOD to the biomass and controlling the concentration of RBCOD in the biomass-substrate mixture produces PHAs having an average molecular weight above 400,000 g/mole.

In a third aspect, the invention provides a method of producing high molecular weight PHAs in biomass including feeding an organic carbon-containing substrate to a PHA-accumulating biomass by intermittently supplying the substrate to the biomass over a period of time, and controlling the frequency and amount of the supply of substrate such that the respiration rate of the biomass does not drop more than 70% relative to the maximum respiration rate achieved by the biomass in response to the most recent supply of substrate.

BRIEF DESCRIPTION OF THE DRAWINGS

With reference to FIG. 5, the actual $\delta_r$ value at the point of fed-batch input is shown as well as the related minimum pulse respiration rate with respect to the maximum rate achieved for the respective substrate inputs.

DETAILED DESCRIPTION OF THE INVENTION

Figure 1:
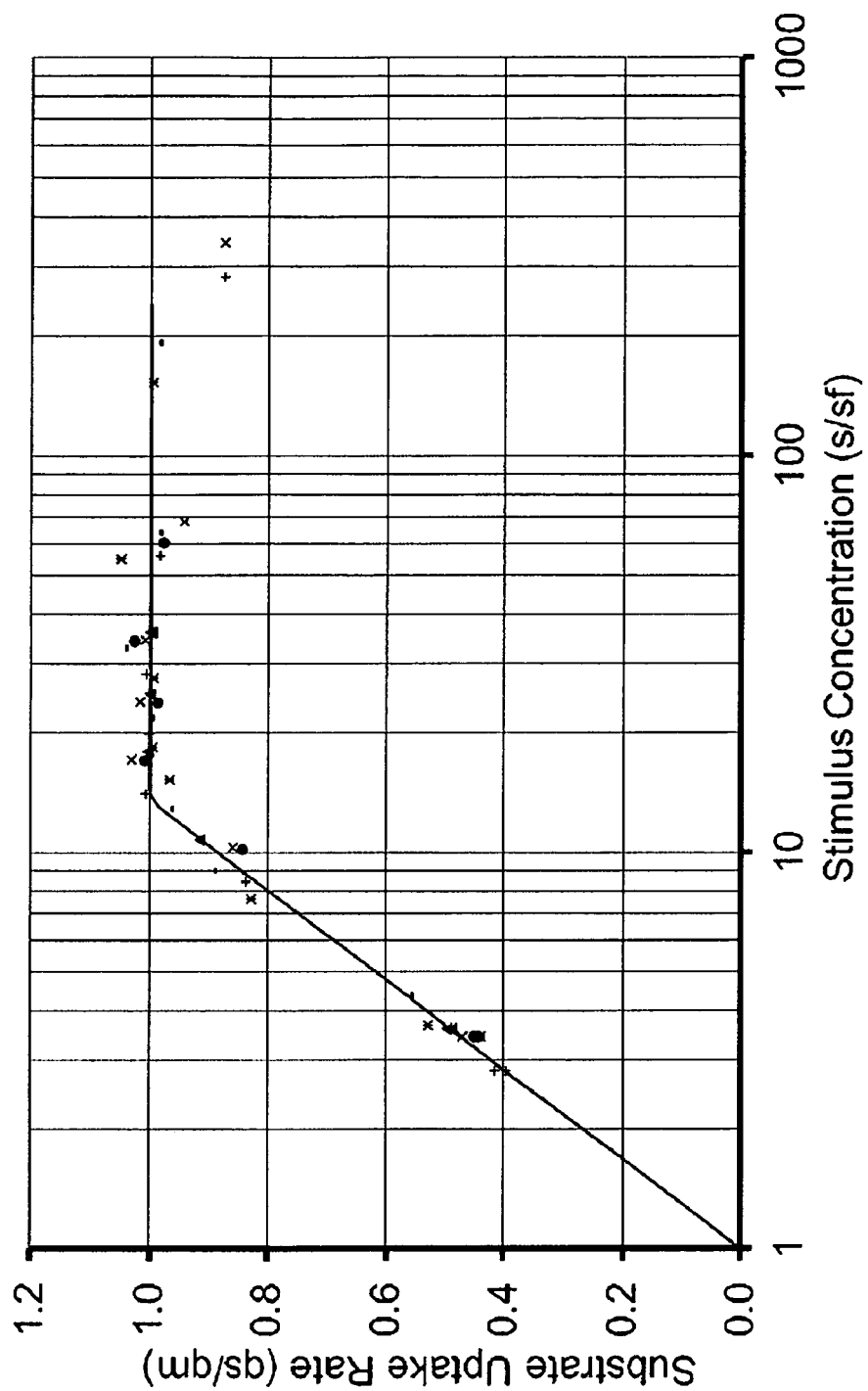
FIG. 1. Normalized experimental data from 6 studies in relation to an empirical model (Equation 1) for the biomass response to a VFA-rich feed stimulus.

The present invention includes novel but practical engineering solutions for the process of accumulation of PHAs in biomass. Objectives that can be satisfied by employing the present invention include:
  Stimulation, sustainment and control of PHA accumulation responses when feeding substrates such as wastewaters with high, moderate and low concentrations of RBCOD;
  Control of a PHA polymerization process in biomass to achieve a high PHA molecular weight;

Saturation or near saturation of the biomass with PHA, where saturation defines the maximum storage capacity of the PAB in the biomass; and Minimal levels of residual RBCOD and other dissolved organic matter remaining in the wastewater by the end of the accumulation process.

Wastewaters are often characterized by organic content in terms of chemical oxygen demand (COD). The total chemical oxygen demand (TCOD) of a wastewater can be further categorized by standard methods in terms of soluble (SCOD) and biodegradable (BCOD) fractions. RBCOD forms part of the soluble COD in a wastewater and can generally be thought as those organic compounds comprising the BCOD that can be assimilated for biomass growth without requiring intervening steps of hydrolysis. The respective concentrations of TCOD, SCOD, BCOD, RBCOD and so forth, in the wastewater, may be reported as mg-COD per liter or mg-COD/L where the mass of COD being reported is with direct reference to the component of organic content being considered. Microbial activity and other forms of physical-chemical processes can be used to increase the soluble, biodegradable, and even the RBCOD fraction of the wastewater TCOD. When the wastewater is suitably characterized and the chemical identity of the RBCOD is known, then the RBCOD content of the wastewater can be explicitly expressed, for example, as total VFAs measured as mg-COD/L. RBCOD can also be operationally defined by standardized methods of respirometry that consider the fraction of the wastewater COD that is rapidly utilized by a biomass when an aliquot of wastewater is pulse fed to the biomass under controlled conditions (Henze et al., 2000). The results of such an operational measurement of RBCOD based on methods of respirometry may vary depending on how well the biomass is acclimatized to the organic compounds that otherwise may be generally understood to be readily assimilated into metabolism of biomass growth, for example RBCOD. The RBCOD of interest for the present invention is the RBCOD which when combined with a suitably acclimated biomass can be assimilated by that biomass and stored intracellularly as PHA.

The RBCOD fraction in wastewater is often dominated by VFAs. VFAs are well established substrates for producing PHAs but other forms of RBCOD are also known to be substrates that mixed cultures can convert into PHAs. The present invention includes PHA production from VFAs and RBCOD in general.

The present invention further provides a fed-batch wastewater treatment process for the biological removal of RBCOD using a biomass that is enriched with PHA accumulating bacteria and the controlled conversion of RBCOD into PHAs. The addition of wastewater to the biomass is controlled so as to achieve a negligible buildup of RBCOD in the mixed liquor by the end of the accumulation process.

Mixed liquor is generally understood to those familiar with the practice of biological wastewater treatment as the mixture of raw or settled wastewater and activated sludge contained in an aeration basin in the activated sludge process. Mixed liquor suspended solids (MLSS) is the concentration of total suspended solids (TSS) in mixed liquor as measured by standard methods, usually expressed in milligrams per litre (mg/L). Mixed liquor volatile suspended solids (MLVSS) is the concentration of volatile suspended solids (VSS) as measured by standard methods, also expressed in mg/L. For the purpose of this invention, the term mixed liquor is used to express the liquid contents of the accumulation process comprising but not limited to suspended solids of active biomass and dissolved solids of RBCOD. Since the biomass in the practice of this invention may be waste activated sludge from a biological wastewater treatment process, the accumulation process mixed liquor is considered and expressed as mixed liquor even before any RBCOD is added for purposes of PHA accumulation.

The addition rate of wastewater containing RBCOD is controlled by using on-line process monitoring. Process monitoring can include strategies of direct measurement of water quality, biomass activity, or biomass characteristics. Process monitoring can also include so-called soft-sensor signals that in combination with specific process knowledge can be used for indirect interpretation of water quality, biomass activity, biomass growth, PHA accumulation, and biomass characteristics. Examples of process monitoring parameters for the process control are as follows:

Ultraviolet/visible (UV/Vis) spectroscopy for indirect indication for substrate concentration (COD), and/or biomass concentration (TSS).

Automated total (or dissolved) organic carbon, or chemical oxygen demand analysis for measurement of dissolved substrate concentration, and/or biomass concentration (VSS).

Respirometry based on, for example, dissolved oxygen, carbon dioxide and/or redox potential measurements for the control of the process aeration and to monitor and respond to changes in the extant biomass respiration rate during sequential fed-batch wastewater inputs.

Hydrogen ion concentration (pH) as a soft-sensor of biomass response and metabolic activity to fed-batch RBCOD inputs.

Turbidometric measurements based on near-infrared backscatter methods for measurement of biomass reflectivity which provides an indirect indication of the PHA accumulation kinetics.

Raman infrared spectroscopy for the direct assessment of biomass PHA content.

Not only quantity but also polymer quality, with respect to a range of chemical, physical, and mechanical properties, is critical to the practical process implementation. The molecular weight and its distribution are principal quality factors that influence polymer mechanical properties. Generally, higher molecular weights and narrower molecular weight distributions are desirable. Sacrifice in molecular weight may be an inherent compromise for economic or more environmentally friendly polymer harvesting from biomass. Polymer processing in a melt is also known to bring further sacrifice to the material properties due to degradation in molecular weight. A higher starting molecular weight after accumulation therefore provides for a greater flexibility in subsequent manipulation of the biopolymer since it is much easier to engineer a controlled decrease in molecular weight than the contrary. One embodiment of the invention is a method to produce PHAs with an average molecular weight ($M_w$) of at least 400,000 g/mol, preferably greater than 600,000 g/mol and more preferably greater than 1,000,000 g/mol.

PHA accumulation in pure culture fermentation as well as in open mixed-culture processes with VFAs is the result of a complex chain of metabolic processes. Not being bound by any particular theory, it is believed that by controlling the rate of one or more of these metabolic processes in the biomass, high average molecular weight PHAs can be produced. For example, the kinetics of PHA accumulation may be considered to be controlled by:

1. $R_t$, The rate of transport of extracellular VFAs into the cell,
2. $R_c$, The rate of conversion of the VFAs into the PHA monomer precursors, and 3. $R_p$, The rate of polymerization of these precursors into PHA.

There is debate as to the extent to which $R_t$ or the flux of VFAs into the cell is actively controlled by the bacteria. Notwithstanding this debate, the transport rate across the cell wall will be influenced by the concentration gradient between extra- and intra-cellular concentrations of VFAs. The intracellular concentration of VFAs will depend on the balance of membrane transport into the cell and the "clearing" rate of intracellular VFAs.

VFAs entering into the cell cytoplasm can be utilized for three possible metabolic functions. The following rates of such functions may be affected by the intracellular VFA concentration:
1. $R_c$, the above mentioned rate of conversion of VFAs into PHA monomer precursors.
2. $R_g$, the rate of anabolic conversion of VFAs for growth of non-PHA biomass. Non-PHA biomass can be in the form of active microorganisms as well as other storage products such as extra-cellular polysaccharides.
3. $R_e$, the rate of catabolic conversion of VFAs into $H_2O$, and $CO_2$ in order to drive metabolic activity for ongoing maintenance, growth and PHA accumulation respiration.

Note that when other non-PHA precursor organic matter is fed to the biomass together with RBCOD such as VFAs, the $R_e$ requirements can be satisfied by this non-PHA precursor source up to 100% of the biomass energy requirements. However, for the case of a RBCOD-only feed, $R_r$, or the removal rate of VFAs from the wastewater, can be assumed to be dependent on $R_g$, $R_p$ and $R_e$ when $R_t$ and $R_c$ are sufficiently rapid:

$$R_r = f(R_g, R_p, R_e)$$

Since the energetic requirements of growth and polymerization are coupled to the rate of biomass growth and/or PHA production, the VFA catabolic rate may be considered to be limited to a function of growth and polymerization rates:

$$R_e = f(R_g, R_p),$$

Therefore, R, depends on $R_g$ and $R_p$ or $$R_r = f(R_g, R_p)$$

This outcome indicates that when $R_t$, and $R_c$ are relatively rapid, the rate limiting steps for VFA removal are $R_p$ and/or $R_g$. If $R_g$ is negligible due to, for example, a period of famine, and/or a limitation of an essential growth element like nitrogen or even oxygen, then the rate limiting step or "bottleneck" for VFA removal is the rate of PHA polymerization or $R_p$. $R_p$ limiting conditions are created when conditions are such that $R_t$ and $R_c$ are, relatively speaking, significantly more rapid than $R_p$ such that $R_p$ is independent of $R_t$, and/or $R_c$. Otherwise stated in theory, $R_p$ limiting conditions or "PHA polymerization limiting kinetics" as used herein, are created when the biomass is able to maintain an intracellular pool of PHA-monomers (substrate) that supply the polymerization process for making PHAs (product), such that the polymerization rate ($R_p$) is unaffected by PHA-monomer concentration. Further, when $R_p$ is the rate limiting step, the kinetics of VFA removal from the mixed liquor is zero order, namely independent of the concentration of VFAs in the mixed liquor.

Considering the aforementioned PHA polymerization kinetics theories, the molecular weights of the PHAs produced in the biomass are predicted to be greater as the probability of chain termination reactions during the accumulation process decreases. According to this model, chain termination probability is minimized by maintaining the level of PHA-monomer precursors during the accumulation process so as to not limit the rate of PHA polymerization. Such level of PHA-monomer precursors may be indicated by zero order VFA removal kinetics, or similarly by the maximum respirometric rate achieved in the biomass and maintained in the biomass during the accumulation process. The kinetics of VFA removal, oxygen consumption, carbon dioxide production, and pH change are examples of parameters that can be monitored in the accumulation process as a means to determine the maximum respirometric rate that has been achieved in the biomass and by what percentage it attenuates subsequent to each supply of RBCOD. Notwithstanding these theoretical interpretations and the potential for other such interpretations, the present invention provides the timing of and supply of sufficient RBCOD to the mixed liquor in order to stimulate a maximum biomass response for PHA accumulation to achieve high molecular weight PHA polymers in parallel with wastewater treatment.

In one aspect, the present invention comprises PHA production with open mixed cultures of biomass for treating waste organic matter. Notwithstanding, the principles and techniques employed by the invention can be used in processes involving pure or constrained mixed cultures of bacteria and/or more refined RBCOD or other feedstocks for biomass and/or PHA production.

Biomass harvested from wastewater treatment facilities can be made to accumulate PHA when fed with RBCOD-containing wastewater. Biomass that is enriched in PHA-accumulating bacteria can accumulate typically in excess of 50% PHA of its total dry weight (active biomass plus PHA). The RBCOD feed should be supplied in order to achieve an initial concentration high enough to stimulate a PHA storage response in the biomass but not too high in concentration so as to cause any form of metabolic inhibition that would be detrimental to the process with respect to polymer yield and productivity.

Although the use of biomass respirometry and fed-batch reactors have become the standard in investigations for assessing PHA accumulation in mixed-culture systems, practical implementation of the technology has not been adequately addressed or demonstrated. For example, a mode of respirometry control for the explicit manipulation and optimization of PHA molecular weight in a fed-batch configuration is still desired.

The present invention provides the controlled addition of RBCOD to the biomass to optimize for higher polymer molecular weight distribution. One aspect of the present invention is a method of producing high molecular weight PHAs in a biomass comprising:
  feeding an organic carbon-containing substrate to a PHA-accumulating biomass by intermittently supplying the substrate to the biomass over a period of time; and
  controlling the frequency and amount of the supply of substrate such that the respiration rate of the biomass does not drop more than 70% relative to the maximum respiration rate achieved by the biomass in response to the most recent supply of substrate.

What defines a sufficiently large pulse volume can be monitored and tuned in real time based on the observed kinetics of the biomass response. The working range will be mass inputs of RBCOD that periodically expose the biomass to peak stimulating concentrations preferably between 20 and 500 mg-COD/L, and more preferably within the range between 40 and 200 mg-COD/L.

RBCOD input amounts can be constant but preferable will be higher initially and attenuated over time as the polymerization kinetics decrease during the PHA accumulation process.

RBCOD inputs to the biomass are provided with sufficient frequency such that the extant biomass respiration rate does not drop more than 70 percent and preferably not more than 30 percent relative to the respiration rate achieved in response to the most recent wastewater RBCOD input.

The acceptable respiration rate decrease for the biomass between RBCOD inputs depends on the number of input events. The greater the number of input events or interruptions the less the extant respiration can decrease between events if molecular weight is to be maximized.

High initial biomass concentration and lower influent RBCOD concentrations may result in a need for increased number of stimulus events.

Biomass concentration increases during a PHA accumulation process due to the mass of PHA accumulation and/or growth of micro-organisms or other non-PHA biomass in the process. A distinction can be made between the total biomass and the active biomass. Active biomass concentration in the accumulation process can be defined as the total biomass concentration (measured as volatile suspended solids) minus the PHA concentration.

PHA average molecular weight may be less affected by the frequency of stimulus events when extant respiration does not decrease more than 30 percent of its extant maximum potential.

Once the biomass becomes saturated with PHA, and in absence of one or more other nutrients essential for growth, the RBCOD may be consumed by the biomass only for cellular maintenance and endogenous respiration. At this point, the PHA productivity diminishes and the RBCOD removal rate becomes significantly reduced. It is usually at this point that mixed culture accumulation processes are terminated. The suspended biomass and water phases are separated and the product is a biomass with high levels of accumulated PHA. However, the effluent from such an accumulation process may contain high levels of residual RBCOD necessitating further treatment before final discharge of the effluent is allowable.

If the biomass becomes saturated with PHA in the presence of all other nutrients essential for growth, the RBCOD may be consumed by the biomass to support processes of non-PHA related growth and maintenance, in addition to concurrent PHA storage. At this stage it is possible to maintain the accumulation process until such point when the PHA mass in the reactor has reached an optimal level and/or buildup of residual soluble COD in the mixed liquor reaches a selected maximum level.

One embodiment of the invention is to drive a PHA-accumulation process in open mixed cultures where the aqueous discharge from the accumulation process is biologically treated at least with respect to its RBCOD content. Another embodiment of the invention is to drive PHA-accumulation processes with real wastewaters where levels of nutrients other than RBCOD used for PHA production promotes a process of combined PHA storage and biomass non-PHA growth metabolic activities.

In practical applications, volume is limiting and represents a significant cost of construction for an accumulation process. Feed-stocks that are good for PHA accumulation may not always be significantly concentrated and therefore, the problem may be to attain sufficient concentrations of RBCOD in order to reach optimum PHA accumulation rates and PHA quality. Lower feed input amounts are in any event more desirable because the higher the feed frequency is, the more opportunities exist for tighter process control, manipulative shifts in feed composition, as well as the avoidance of excess RBCOD in solution at the end of the PHA accumulation batch run. Fed-batch operation with a higher frequency of fed-batch inputs begins to approach conditions of a continuous feed strategy. As the frequency of feed increases the distinction between a fed-batch and a continuous feed strategy become blurred. Thus the volumetric feed rate rather than the dose input frequency becomes an equivalent parameter in the control and process operation.

Fed-batch operation can be accomplished by distinct dose inputs of selected volume applied to all the biomass in a completely mixed reactor. Fed-batch operation can also be accomplished by bringing the biomass in a side stream or within distinct reactor zones in contact with RBCOD input such that organisms in the biomass experience distinct stimuli of substrate supply and distinct periods of substrate interruption. When the biomass is brought in contact with substrate either within a well-mixed reactor or within zones or side streams, the feed may be supplied in pulses or continuously. A feed interruption may be defined by conditions where the microorganisms in the biomass experience feed supply reduction in time or space due to being exposed to an environment where a negative gradient in substrate concentration exists. Thus, the concept embodied in the present method for accumulating PHAs in biomass entails pulse feeding as well as feed interruptions. Certain terms are used herein to describe both pulse feeding and feed interruptions. For example, "intermittently supplying the substrate to the biomass" or "interrupting the feed" includes pulse feeding as well as providing for feed interruptions and specifically includes pulse feeding the substrate to the biomass or circulating a portion of the biomass from a zone having a relatively low concentration of substrate to a zone having a relatively high concentration of substrate while the substrate is fed continuously or non-continuously. In either case the method or process is intermittently supplying substrate to the biomass.

In one embodiment of the invention the PHA accumulation process is continued until practical limitations are reached, feeding targets have been achieved, signs of saturation for PHA-accumulation are apparent, and/or the total mass of PHA in the reactor has reached a targeted level. Indications of these events include:

Practical limitations including physical constraints of the reactor such as available tank volume for fed-batch operation with variable reactor liquid volume.

Practical limitations including constraints in kinetics of biomass separation from discharged effluent for fed-batch operation with constant reactor liquid volume.

Feeding targets including the addition of wastewater RBCOD based on established or case-specific observed norms of the biomass conversion yields which may vary from wastewater to wastewater. For example, a typically observed conversion yield for a fermented dairy wastewater is 0.4 kg-PHA produced per kg-VFA-COD consumed. Therefore, if the biomass is with known capacity for PHA accumulation to 100% of the initial biomass dry weight, then the targeted wastewater addition would be 2.5 kg-COD per kilogram of initial biomass.

Signs of saturation or an end-point in PHA accumulation including any or all of the following measureable signals:

An onset of a buildup of RBCOD in the accumulation reactor remaining after each fed-batch input.

A decrease in the substrate uptake kinetics below an established threshold value that will be specific to the kind of wastewater used.

An observed saturation of PHA in the biomass using on-line assessment of biomass reflectivity as the indicating parameter.

An observed target of PHA volumetric productivity, using combined on-line assessment of biomass PHA content (reflectivity) and biomass concentration (mixed liquor turbidity) for cases where biomass growth and PHA storage occur simultaneously.

A decrease in the biomass respirometry to below an established threshold value that may be specific to the kind of wastewater used.

An observed shift of the biomass respirometry towards response from the organic inputs in the fed-batch wastewater to a response to, for example, the nitrogen inputs in the wastewater.

The time required for biomass to accumulate its maximum potential in PHA may vary from batch to batch. Fluctuations may occur with respect to kinetics and other characteristics of the mixed culture process due to, for instance, microbial population dynamics, shifts in metabolic condition (physiological state) and variations in influent feed characteristics. Suitable PHA accumulation feed-stocks can include feed-stocks selected from RBCOD sources other than those resident in the wastewater used to produce the PHA-accumulating biomass. Such disparate feed-stocks may enhance the overall process economics or may tailor the RBCOD composition for producing different kinds of PHAs.

Determination of Fed-Batch Conditions for PHA-Accumulation

Experiments were conducted with activated sludge biomass that was enriched for PAB based on aerobic feast-famine selection in two 4 liter laboratory scale sequencing batch reactors (SBRs). The SBRs were operated as parallel biological wastewater treatment processes. A fermented dairy industry wastewater was used as the feed for the PAB-rich biomass production. The fermented dairy wastewater COD was comprised approximately 90% of VFAs. The fermented wastewater was supplemented with macro and micro-nutrients in excess of metabolic requirements for the activated sludge. The SBRs were operated with a 1 day hydraulic retention time (HRT) and a 4 day solids retention time (SRT). The 1 day HRT was based on 2×12 hours cycles per day where a cycle was defined with a starting point of 2 L reactor mixed liquor volume. At the start of the cycle 2 L of wastewater were rapidly fed under aerobic conditions. The wastewater and mixed liquor were reacted aerobically with dissolved oxygen levels in excess of 1 mg-$O_2$/L for approximately 11 hours. Subsequently, aeration and mixing were stopped and the activated sludge in the mixed liquor was allowed to settle for 30 minutes under quiescent conditions. After settling 2 L of supernatant were decanted. In one of every 2 cycles 500 mL of mixed liquor were pumped out (wasted) for the SRT control just before aeration and mixing were stopped for sedimentation. When activated sludge was wasted from the reactor only 1.5 L of supernatant were decanted. The feast-famine cycle was no more than 2 hours of feast directly after feeding, followed by not less than 9 hours of famine as assessed through both replicate and detailed experimental cycle-studies and routine dissolved oxygen monitoring. The reactors supported a steady state concentration of approximately 2 g/L of activated sludge. A similar system was also operated at pilot scale whereby one SBR with a working volume of 400 L was used.

In one set of replicated experiments spanning approximately 3 months of SBR operation, the wasted biomass was subjected to pulse inputs of either concentrated acetic acid or the fermented dairy wastewater. The objective was to measure biomass response to a "feast" stimulus under conditions where extant PHA content in the biomass was negligible. The biomass response to these substrate inputs was monitored based on dissolved oxygen trends and also based on more detailed water quality analyses over the course of the biomass response to respective pulse inputs of organic substrate. The biomass response could be modeled by a function of form (FIG. 1):

$$q_s = \begin{cases} k_s \ln\left(\dfrac{s}{s_f}\right), s \geq s_f & \text{and } k_s \ln\left(\dfrac{s}{s_f}\right) \leq q_m \\ q_m, s \geq s_m & \text{and } k_s \ln\left(\dfrac{s}{s_f}\right) > q_m \end{cases} \qquad \text{Eqn. 1}$$

$$R_r = q_s X \qquad \text{Eqn. 2}$$

where, $q_s$=the specific substrate consumption rate (mg-COD/g-biomass/minute)

$k_s$=the biomass response factor to a substrate stimulus s=the substrate initial concentration providing the stimulus (mg-COD/L)

$s_f$=the estimated threshold substrate concentration for a measureable biomass response $s_m$=the substrate concentration achieving a maximum response in substrate consumption $q_m$=the maximum estimated specific substrate consumption rate X=the biomass concentration $R_r$=rate of removal of substrate from solution Deviations from the model at higher stimulus concentrations are believed to be due to PHA accumulation in the biomass after a series of stimuli. Once the biomass was stimulated by the VFA pulse input, the VFA removal rate ($R_r$) was observed to follow zero order kinetics to well below the estimated $s_f$ concentration, and thus $q_s$ was approximately constant after each of the respective stimulated response level (s). This outcome indicated that sufficient substrate ($s_f$) was required to stimulate a measureable feast response, and the metabolic response was sensitive to the level of stimulus (s) for stimuli that were below the concentration $s_m$. However, once the response was established it was sustained until the added VFAs were essentially all consumed.

Although the observed trends from such experiments were consistently reproduced, the magnitude of the response in replicated studies on different days was found to be variable. The concentration $s_m$ ranged from 40 to 115 mg-COD/L. In direct proportion, $s_f$ ranged from 3 to 9 mg-COD/L and $q_m$ ranged from 8 to 21 mg-COD/g-biomass/minute. If these experimental results are to be considered typical, then fed-batch VFA additions achieving in excess of approximately 150 mg-COD/L should be sufficient to drive the process of PHA accumulation such that the accumulation process kinetics are limited only by the intracellular rate of PHA polymerization.

However, lower fed-batch WA additions achieving down to as low as 40 mg-COD/L may also be adequate depending on the extant physiological state of the biomass for PHA polymerization. Lower additions will also be possible when the biomass contains significant levels of PHA because polymerization kinetics may decrease in step with biomass PHA content. Since $q_m$ is observed to be related to $s_m$, the kinetics of the biomass response to an initial pulse of, for example, 200 mg-COD/L could be used to assess in real time the minimum WA mass additions required to achieve polymerization limited PHA accumulation kinetics. Therefore, the respirometry kinetics can be used as direct feedback to the requisite mass additions for a fed-batch PHA accumulation process.

The amount of VFA used to stimulate theoretical PHA polymerization limiting kinetics can vary. Based on our current body of experimental results, a conservative RBCOD-pulse input would be one that achieves an initial stimulus level of 200 mg-COD/L for biomass with negligible stored PHA.

Since $s_m$ and $q_m$ are directly coupled, the kinetics of substrate consumption can be used to establish $s_m$ in real time through online monitoring during an accumulation process. The concentration $s_m$ that needs to be added to maintain theoretical PHA polymerization limiting kinetics is expected to decrease in step with the accumulation process because as the biomass accumulates PHA, the theoretical rate of PHA polymerization decreases.

The Use of Respirometry for Fed-Batch Control

Figure 2:
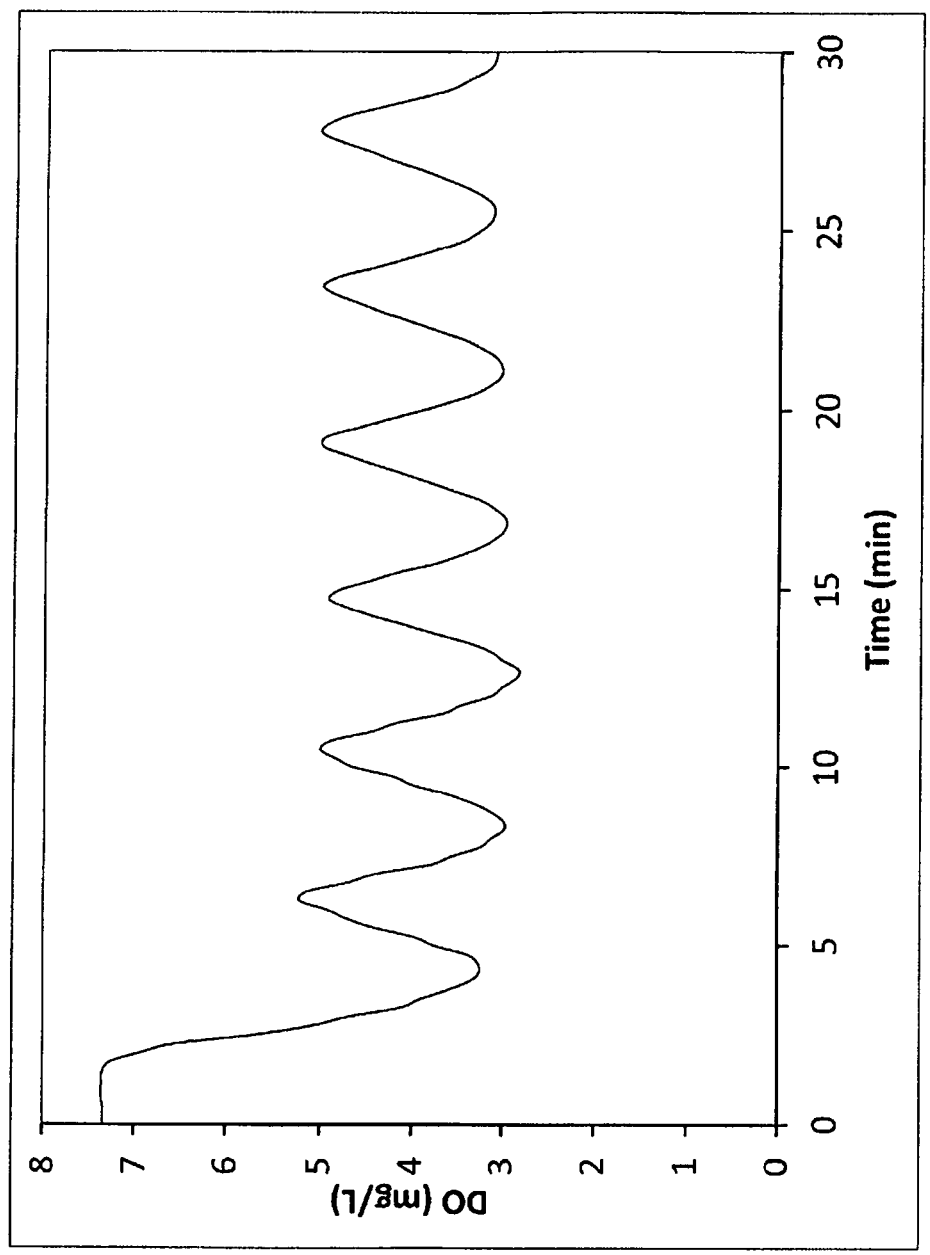
FIG. 2. Representative dissolved oxygen (DO) concentration signal used to control automatic substrate addition (Equation 3) in experiments for PHA accumulation in PAB-rich biomass with pulses to achieve a constant stimulus of 100 mg-COD/L of VFA.

We undertook a number of sets of accumulation experiments using a concentrated fermented dairy wastewater and pure VFA mixtures as feed in aerobic fed-batch reactors used for laboratory and pilot scale PHA production with biomass enriched in PHA-accumulating bacteria coming from the SBR wastewater treatment systems described above. The fed-batch reactors were operated with sequential inputs of WA rich wastewater with a dissolved-oxygen (DO)-based control strategy producing typical trends in dissolved oxygen as shown in FIG. 2.

Using the DO-based control strategy, theoretical PHA polymerization limiting kinetics were assumed according to previously mentioned experimental results for conditions for pulse fed-batch PHA accumulation. The initial VFA concentration after each input was nominally 200 mg-COD/L. Fed-batch inputs were controlled from on-line monitoring of dissolved oxygen (DO) concentrations. For conditions of constant mixing, constant aeration and constant gas-liquid mass transfer of oxygen, changes in DO could be related to underlying changes in the biomass respiration rate. A shift down in DO indicated a relative increase in biomass respiration rate and a shift up in DO indicated a relative decrease in biomass respiration rate. The control strategy was as follows:

a. A steady state DO level was established before the first VFA input. This reference DO level ($DO_r$) established a reference for the initial background (endogenous) respiration rate for the biomass with negligible PHA content.
b. for each respective fed-batch VFA-input stimulus, the maximum rate of biomass respiration was indicated by the minimum DO level achieved ($DO_m$).
c. A subsequent VFA-pulse input was triggered by a relative increase in DO representing a decrease in biomass respiration rate due to substrate depletion. After each $DO_m$ was determined, a relative increase in DO in time ($DO_t$) above a pre-determined critical threshold ($\delta^*$) was used to trigger a subsequent single pulse input from the VFA-feed pump as follows:

feed next after $DO_m$ is estimated when $\delta_t = \frac{DO_t - DO_m}{DO_r - DO_m}$ exceeds $\delta^*$     Eqn. 3 d. Accumulations were run for set times and with varying amount of initial biomass concentrations. Accumulation times in these experiments ranged from 5 to 20 hours.

In one set of experiments the accumulation process was controlled with a $\delta^*$ of nominally 0.35. The number pulse was adjusted by using different pulse concentrations (20-500 mg-COD/L) and different DO concentrations (0.1-3.0 mg/L) at maximum respiration rate.

Figure 3:
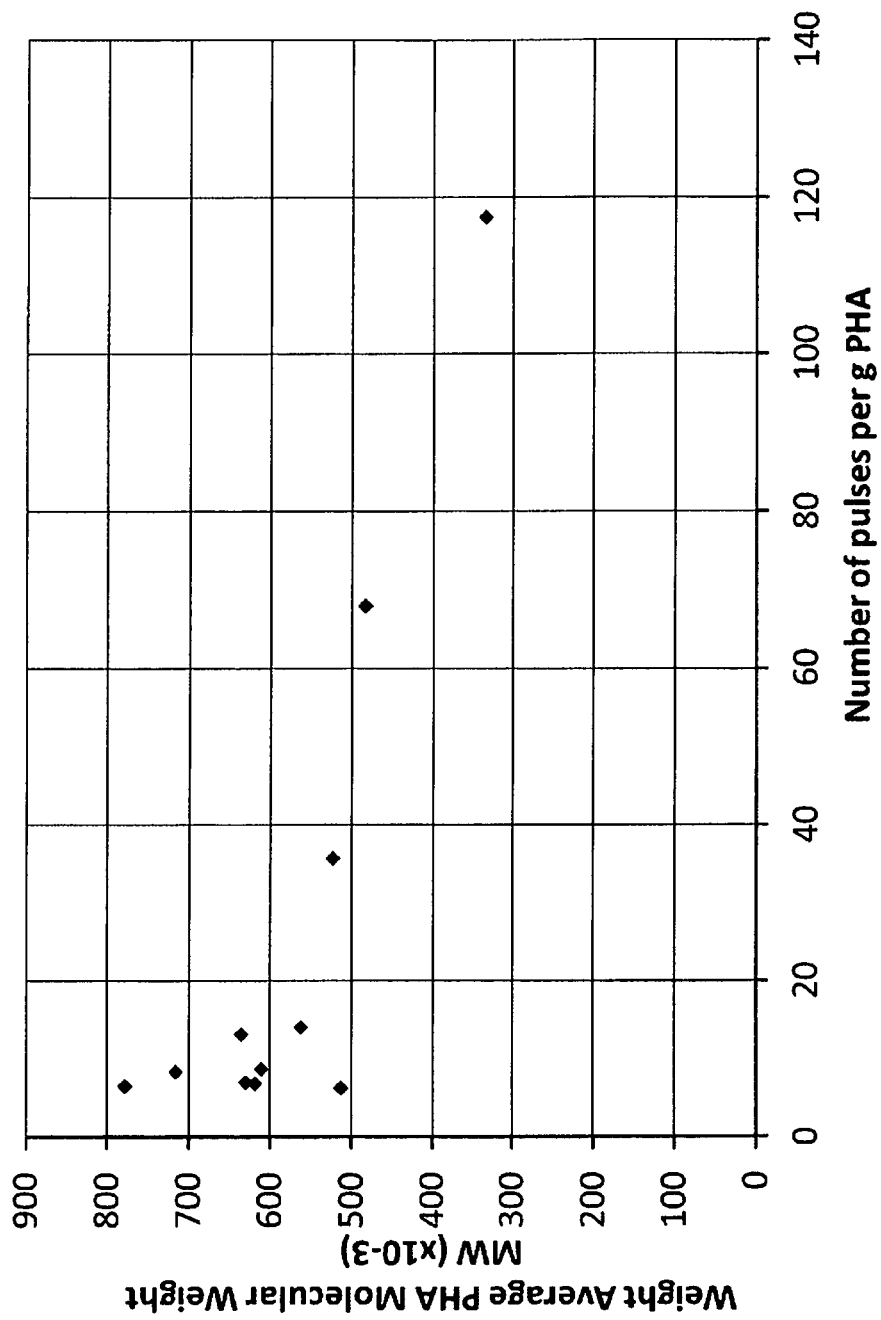
FIG. 3. Results from replicate accumulation experiments using a concentrated fermented dairy wastewater as substrate for fed-batch accumulation of PHA.

The number of fed-batch inputs was observed to influence the resultant molecular weight of the PHA polymer (FIG. 3). At the same time a degree of variability in molecular weight was observed in the region of reduced fed-batch inputs. This variability could be attributed to different aeration conditions that would result in different outcomes for respirometry shifts given the same nominal $\delta^*$ used according to the process control. Therefore, explicit maintenance of biomass respiration (as opposed to DO in equation 3) in fed-batch control is significant and becomes ever more significant the greater the number of fed-batch inputs. In order to maintain the feed input such that RBCOD concentrations are as low as possible, more fed-batch input events are necessary. Similarly, the higher the concentration of active biomass in the reactor the more fed-batch inputs will be necessary to maintain the desired biomass respiration.

Figure 4:
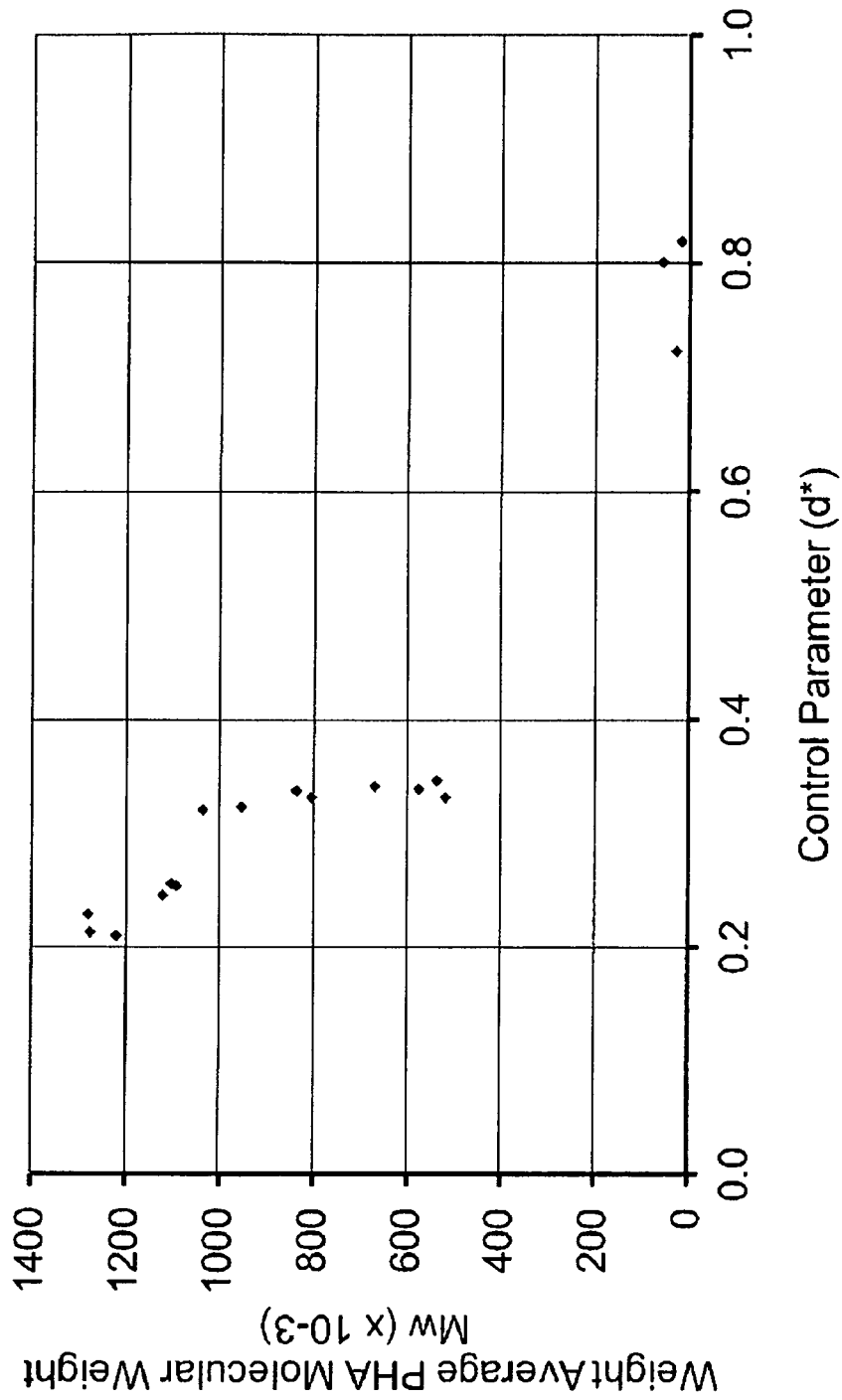
FIG. 4. Results from replicate accumulation experiments using a concentrated fermented dairy wastewater as substrate for fed-batch accumulation of PHA.

In a different set of experiments run under similar conditions but over a range of selected $\delta^*$, the lower $\delta^*$ values for fed-batch accumulation involving many fed-batch inputs to the biomass tended to result in higher PHA molecular weight by the end of the accumulation. The feed pulse inputs achieved a pulse-initial concentration of 200 mg-COD/L and the control parameter is defined by Equation 3 (FIG. 4). Similar to the results in FIG. 3, a high degree of variability was observed in the region of $\delta^*$ between 0.3 and 0.4 (FIG. 4).

Figure 5:
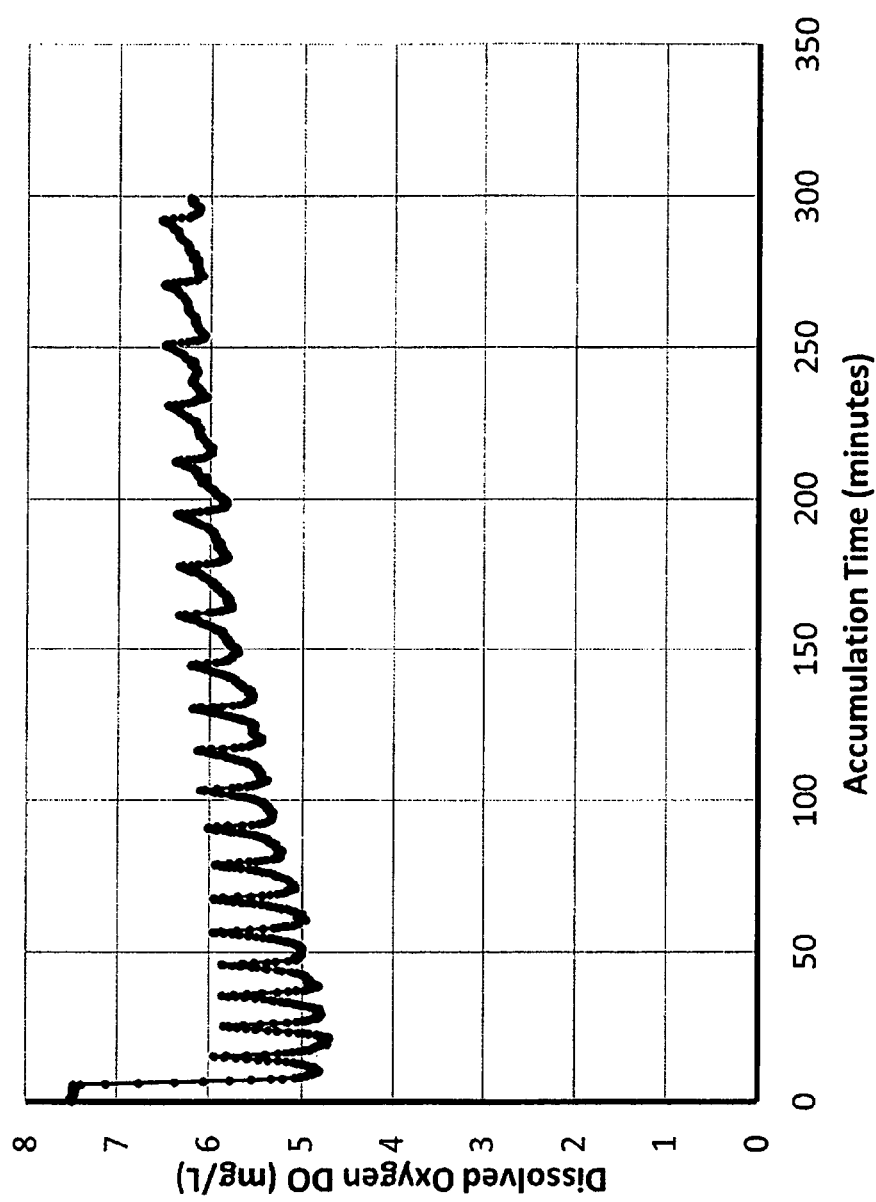
FIG. 5. Typical dissolved oxygen trend for accumulation of PHA on PAB-rich activated sludge using a fermented dairy industry wastewater as substrate for PHA.
Figure 6:
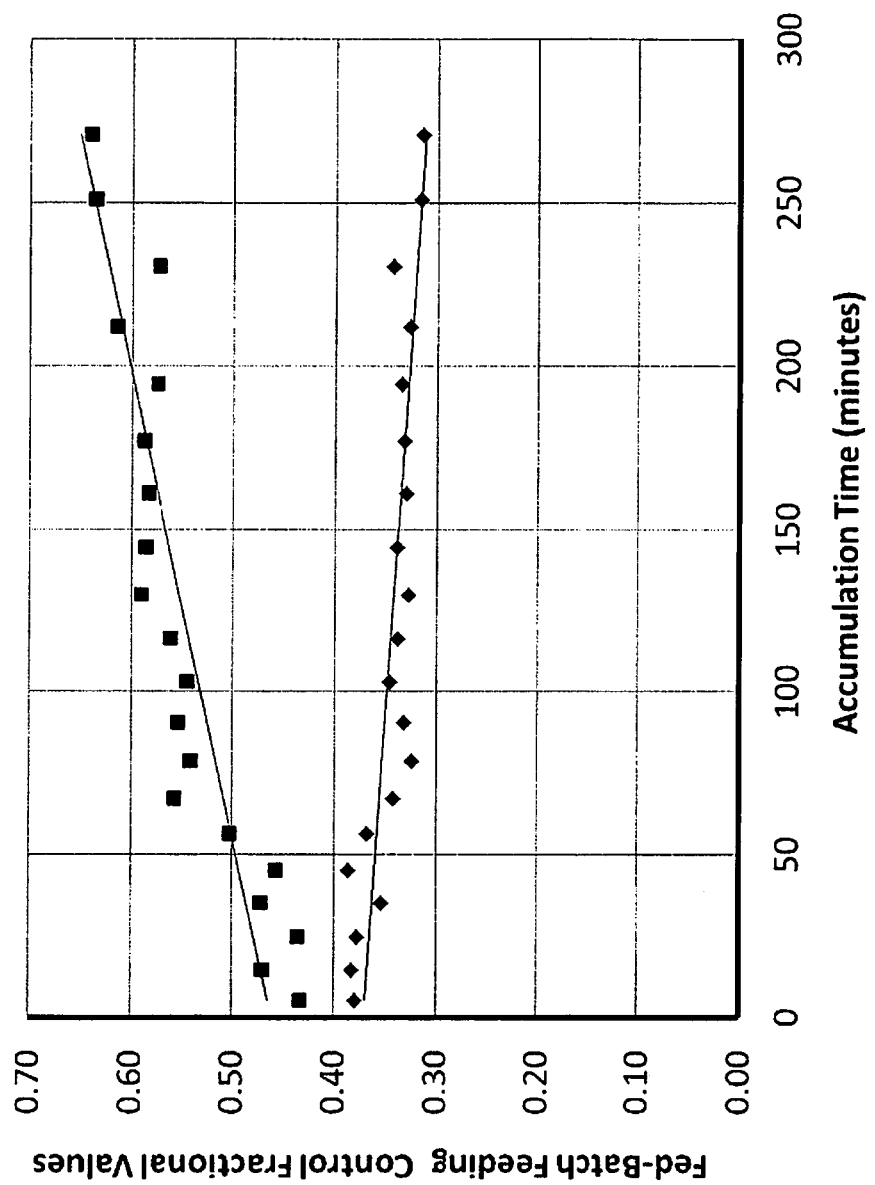
FIG. 6.
Figure 7:
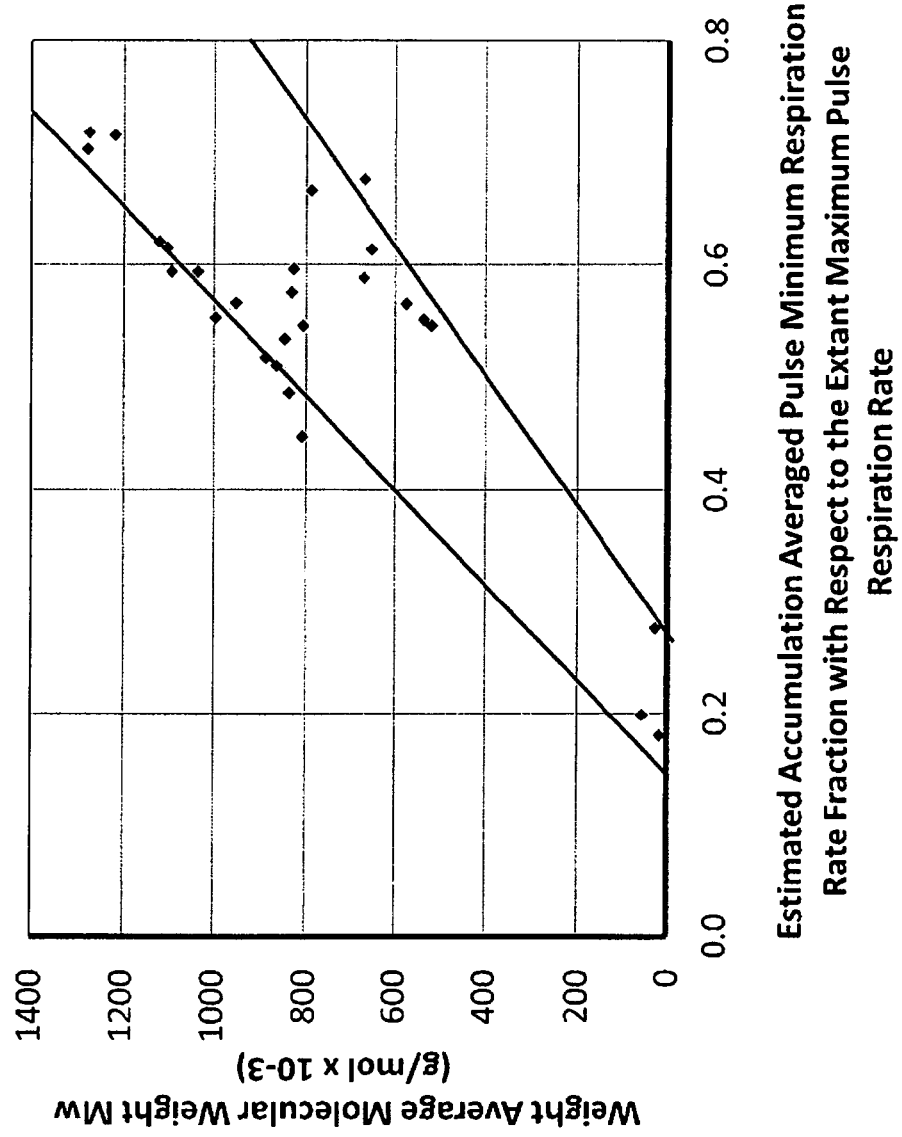
FIG. 7. Summary of accumulation results of numerous experiments considering the resultant estimated average pulse minimum respiration rate reported with respect to the extant maximum pulse respiration rate, and weight average molecular weight of the PHA accumulated.

Generally, the greater the number of fed-batch inputs, the more significant the maintenance of polymerization kinetics is for achieving higher final PHA average molecular weight reported as $M_w$. In experiments where the aeration oxygen mass transfer kinetics could be estimated, an oxygen mass balance was undertaken and biomass respiration shifts from feed pulse stimulation and interruption were determined explicitly. Thus, the average extant decreases in respiration corresponding to selected $\delta^*$ threshold values were estimated for each fed-batch accumulation experiment (FIGS. 5, 6 and 7). In FIG. 5, each fed-batch input corresponds to a trend of reduced DO to a minimum value. The trigger for each fed-batch input was according to Equation 3, and for this accumulation a set point of $\delta^*$ of 0.3 was used.

While the observed variability indicates that other factors contribute to the final PHA average molecular weight, the average decrease in biomass respiration rate between fed-batch input events is a substantial controlling parameter. In one embodiment of the invention, the biomass respiration rate is maintained at more than 30 percent of the extant maximum. In a preferred embodiment, the biomass respiration rate is maintained in excess of 40 percent of the extant maximum. In a more preferred embodiment, the average biomass respiration rate is maintained in excess of 70% of the extant maximum. Up to a 30 percent decrease in relative respiration rates between fed-batch input events is preferred so as to reduce the negative impact of increased theoretical chain termination probability during the PHA accumulation process. A high probability of chain termination during PHA accumulation in biomass is generally understood to result in lower average molecular weight.

In one embodiment, fed-batch input control is based on a respiration trigger point rather than solely on dissolved oxygen. FIG. 6 illustrates how selection of a fed-batch input trigger based on equation 3 translated to a corresponding relative decrease in relative respiration between RBCOD stimulus events. The $\delta^*$ set point under estimated the actual δ* upon feeding due to delay in the feed-back and control (♦). Differences between set and actual δ* values were highest in the beginning of an accumulation due to the fact that the biomass was more active at the start of an accumulation. Corresponding to the actual δ* values the resultant relative decrease in extant respiration rates before the next feed-input was estimated (■)

In a preferred embodiment of the present invention, the fed-batch input control is quantitatively calibrated to actual respirometry rate shifts for the biomass.

Determination of PHA Molecular Weight

Average molecular weight reflects the average size of the polymer chain lengths. In most cases PHA is a polymer with a relatively broad molecular weight distribution. $M_n$ is the number average molar mass and it is defined as:

$$M_n = \frac{\sum N_i M_i}{\sum N_i} \qquad \text{Eqn. 4}$$

where $N_i$ is the number of molecules with molar mass $M_i$. The weight average molar mass, $M_w$, is defined as:

$$M_w = \frac{\sum N_i M_i^2}{\sum N_i M_i}. \qquad \text{Eqn. 5}$$

The polydispersity index (PDI), a measure of the molecular weight distribution, is defined as:

$$PDI = \frac{M_w}{M_n} \qquad \text{Eqn. 6}$$

$M_w$ is always larger than $M_n$ so the PDI will always be greater than 1. PDI for PHA-resin is typically around 2 and $M_w$ has been observed to generally range from 10,000 to 3,000,000 Da. Molecular weight distribution can be influenced by the method of accumulating PHA in the biomass, the method for recovering the PHA resin and the method of further processing the resin into end-user products.

PHA was extracted from distilled water-rinsed and dried biomass with acetone (20 mg-biomass containing nominally 10 mg-PHA per mL acetone) at 125° C. for 2 hours. The extracted polymer in acetone was decanted from the residual biomass and the solvent was evaporated.

Molecular weight distribution (referenced to polystyrene standards) of the extracted polymer was determined by size exclusion chromatography (SEC): The SEC was performed with a pump (Viscotek VE 1122), a dual refractometer/viscometer-detector (Viscotek Model 250) and three linear columns coupled in a series (Shodex KF-805, Shodex KF-804 and Shodex KF802.5). The detector temperature was 37° C., while the studies were carried out at room temperature. The solvent used was chloroform (Merck pro analysis >99%) having a flow rate of 1 ml/min. The injection volume was 100 μL.

Molecular weight was calibrated with reference to four different polystyrene standards with known average molecular weights of 1,800, 650, 96 and 30.3 kg/mol, respectively. The detector measuring the refractive index was used to examine the signal of the standards and the samples.

The sample examined by SEC was dissolved in chloroform to a concentration of 5 mg/mL at 100° C. for 10 minutes. Before injecting the sample into the column the polymer solution was filtered (PALL Life Sciences Acrodisc® CR 25 mm Syringe Filter with 0.45 μM in pore size). From the resolved distribution of molecular weight for the PHA from each sample, the characteristic quantities of $M_w$, $M_n$ and PDI were calculated.

The weight average molar mass (weight) or $M_W$ has been the adopted metric for PHA molecular weight for the present invention.

Determination of Maximum Molecular Weight and Accumulation Rate

As outlined above, a challenge for fed-batch PHA accumulation is to achieve the maximum molecular weight by sustaining a high rate of polymerization with low chain termination probability. The following methodology can be used to determine the expected maximum molecular weight and accumulation rate that is obtainable for a particular biomass under a particular set of environmental conditions. This maximum can serve as a point of reference for fed-batch accumulations that are conducted with the same biomass and RBCOD combination under more readily achievable fed-batch conditions in a larger scale system.

Biomass with substantial potential for PHA-accumulation but with a low initial PHA content (below 5% of the total suspended solids) is used. The biomass is adequately stirred and aeration is provided such that the concentration of dissolved oxygen is always above 2 mg/L.

Carbon substrate in the form of RBCOD is added to the biomass such that a substantial amount of PHA is produced without the need of more than three fed-batch inputs of substrate. Thus, the concentration of RBCOD exposed to the biomass will not go below 100 mg/L more than a maximum of three times during the course of the accumulation experiment. These feeding interruptions are systematically kept to a minimum using, for example, the control strategy of equation 3. Adequate fed-batch input concentrations of RBCOD are in the range 0.5 to 2 g/L.

The molecular weight of the PHA extracted from the biomass at the end of such an experiment can reference the practically achievable maximum obtainable with the given biomass and substrate combination. The highest specific rate of PHA accumulation observed over the course of such an experiment (expressed as g-PHA per g-'active biomass' per hour) can be used to indicate the maximum rate of PHA accumulation of the biomass under representative environmental conditions. (See, for example, Lemos et al., 2006, Serafim et al., 2004, Serafim et al., 2008). Higher PHA molecular weight appears to be associated with maintaining, on average, higher respiration rates in between events of fed-pulse stimuli as shown in FIG. 7.

Determination of the End Point in an Accumulation Process

When open mixed cultures of PAB-rich biomass have accumulated PHA produced with RBCOD derived from wastewater, it is not always possible to maintain PHA storage as the dominant metabolic activity. If the wastewater contains other essential nutrients required for non-PHA microbial growth, then a fraction of the RBCOD may be consumed to increase the amount of active biomass. Therefore, during PHA accumulation processes both intracellular PHA storage and microbial growth may ensue concurrently. Microbial growth response may increase over the course of the PHA accumulation process but increased growth response does not necessarily mean a decrease of PHA accumulation in the biomass. For example, in several experiments a PHA accumulation process was performed with PAB-rich biomass and fermented dairy wastewater that is restricted in nitrogen content but still contains sufficient nitrogen, phosphorus and other trace nutrients to support a non-PHA growth response in the biomass during the PHA accumulation process. The biomass achieved a nominal PHA content of 50% of the total suspended solids, but after that point combined growth and PHA storage lead to an overall increase of both active biomass and PHA content. The relative PHA content of the biomass remained constant or increased slightly. In such cases a high respirometry in the biomass continues long after a maximum PHA content has been achieved since the total biomass in the process continues to increase. In contrast, when the same biomass is fed with a wastewater containing only RBCOD, the biomass respiration response to RBCOD input has been observed to attenuate dramatically once the maximum amount of PHA is accumulated. Since the practice of PHA production from RBCOD in wastewater should accommodate wastewater with RBCOD as well as presence of other nutrients, respiration rate alone may not provide for a sufficient indication towards defining a process end-point or termination criteria. It has been observed that PAB-rich biomass may exhibit the same capacity for PHA accumulation but with variable accumulation kinetics, thus fixed duration may also not be sufficient criterion for this fed-batch process.

Figure 8:
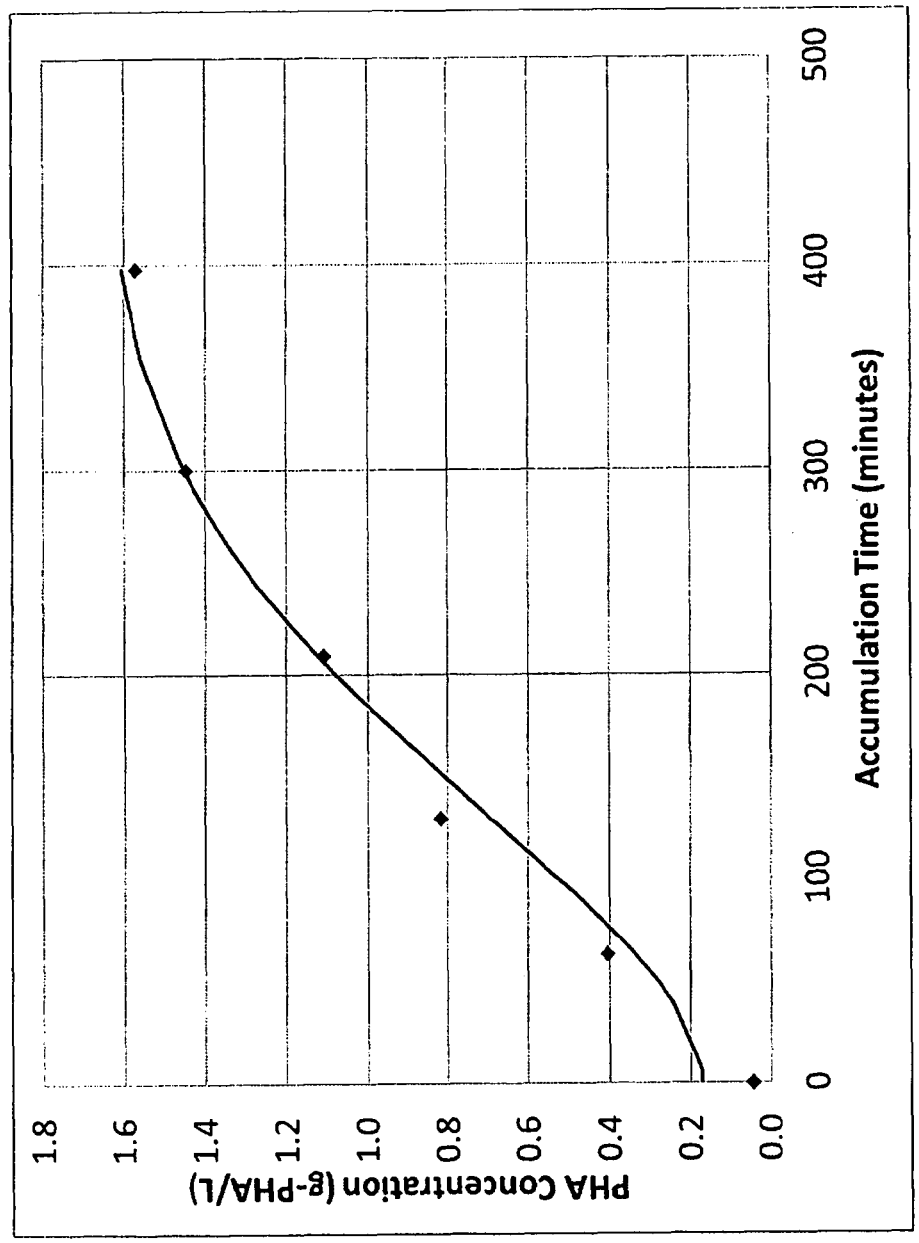
FIG. 8. Representative results of pilot scale (100 L) accumulation of PHA in PAB-rich biomass using a fermented dairy industry wastewater as substrate.

The inventors have found that the biomass reflectivity or color changes upon PHA accumulation. This color change appears to be a direct correlation to the amount of PHA contained within the biomass. Therefore, in one embodiment, the method of the present invention includes the monitoring of the mixed liquor suspended solids concentration as well as the relative change in suspended solids reflectivity (color) to follow the PHA accumulation process. In a preferred embodiment, biomass reflectivity or color change is monitored with the technique of light back-scatter at near infrared wavelengths. An example of such monitoring data is provided in FIG. 8. In FIG. 8, the initial biomass concentration was 1.5 g-VSS/L and feed pulse inputs resulted in a theoretical nominal maximum RBCOD concentration of 55 mg-COD/L for each feeding event. A total of 81 fed-batch inputs were made with an average actual $\delta^*$ of 0.22 (equation 3) which served to maintain the respiration rates on average at 59% of the extant maximum. Six grab samples were taken during the accumulation and PHA concentration in these samples were assessed by established methods of GCMS quantification (♦). The trend line reports the on-line monitoring signal of back-scatter turbidity measurement using near-infrared light at 880 nm.

In order to maximize the recovery of desired PHAs from a PHA accumulation process, the process can be terminated upon one or more thresholds being achieved. Through the combined measurement of process respirometry, reactor PHA content, and residual RBCOD, the termination criteria can be established related to practical process capacity, wastewater discharge limits, PHA-volumetric productivity, PHA yields on substrate and the like. One skilled in the art can recognize the practical, technical, economic and/or environmental performance constraints for determining when to terminate a PHA accumulation process.

EXAMPLES

The following examples are illustrative of the methods and processes of the present invention and are not to be construed as limiting thereof.

The PHA accumulation process described in these examples and throughout the specification can be carried out as a part of a biological wastewater treatment process, or as an adjunct to a wastewater treatment process, or entirely separate from a wastewater treatment process. In a typical biological wastewater treatment process, wastewater influent or a wastewater stream is directed into a wastewater treatment system that typically comprises one or more reactors, a solids separator, and other complimentary components. Activated sludge is used to biologically treat the wastewater influent. Typically the activated sludge is mixed with the wastewater influent to form mixed liquor and the mixed liquor is biologically treated. Typically the mixed liquor is subjected to aerobic, anoxic, and/or anaerobic conditions to carry out various biological treatment processes. For example, it is known to biologically treat wastewater to remove BOD, COD, phosphorus, nitrogen and other contaminants. A solids separator such as a clarifier is used to separate the activated sludge from the wastewater and the separated activated sludge is recycled and mixed with incoming wastewater influent while a portion of the activated sludge is wasted.

The biomass that forms a part of the activated sludge or waste activated sludge can then be utilized in the PHA accumulation processes described herein. Here the biomass is separated from the activated sludge or the waste activated sludge and directed to one or more reactors where the PHA accumulation process is employed. The feed for the biomass can be taken from the wastewater influent which typically includes RBCOD. There are cases where the RBCOD concentration or the type of RBCOD in the wastewater influent is not appropriate for the PHA accumulation process. Therefore, in certain cases the biomass is fed with an alternative or augmented wastewater stream or another feed stream having an appropriate concentration and type of RBCOD.

Figure 9:
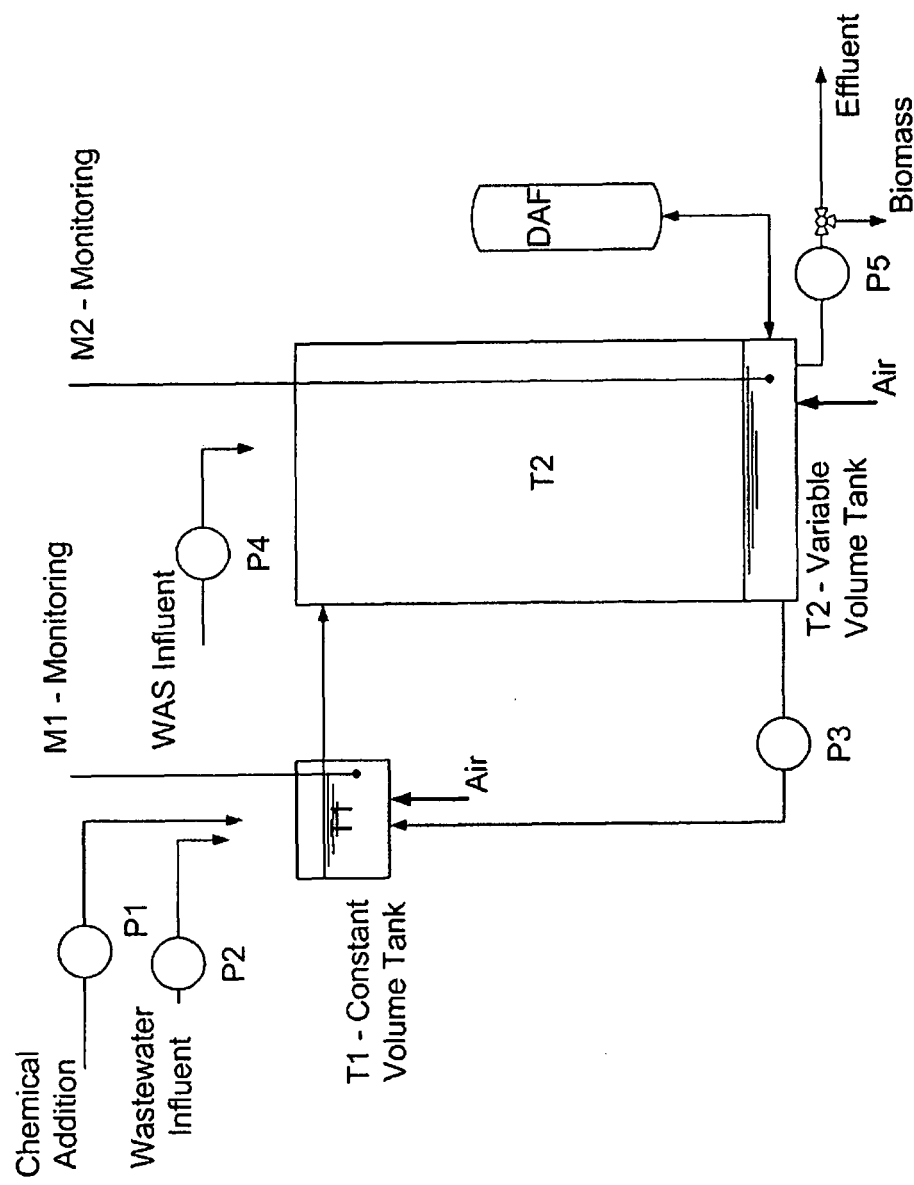
FIG. 9. Representative example of a variable volume aerobic PHA accumulation process.
Figure 10:
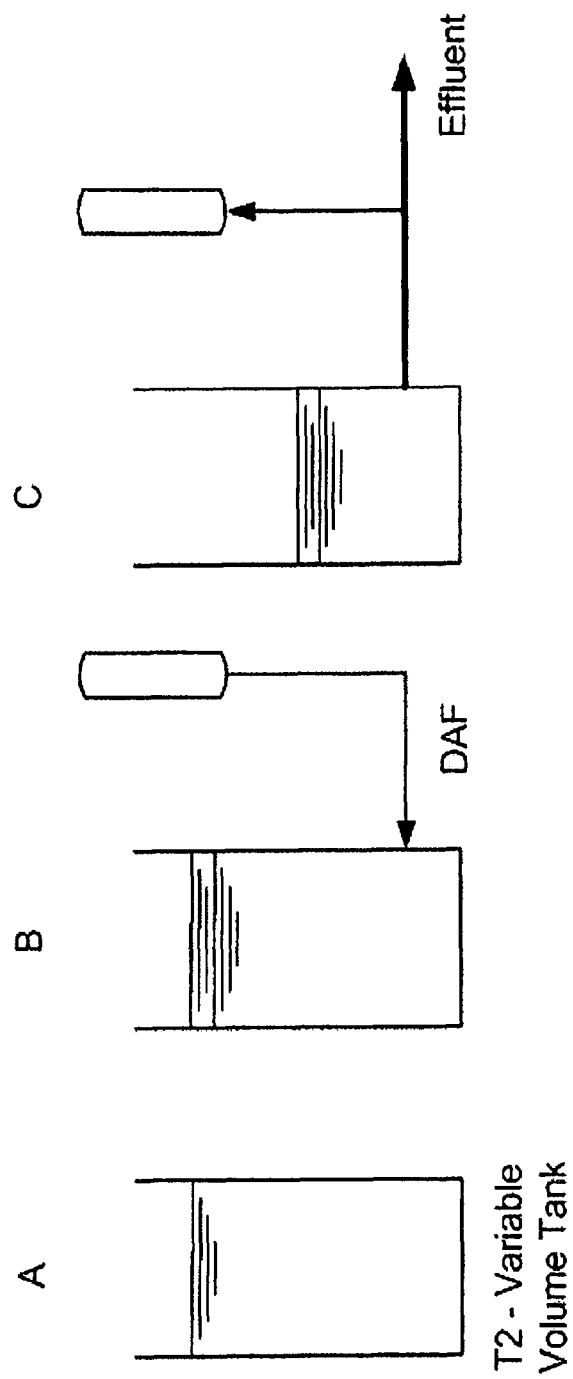
FIG. 10. Representative example of a variable volume aerobic PHA accumulation process.
Figure 11:
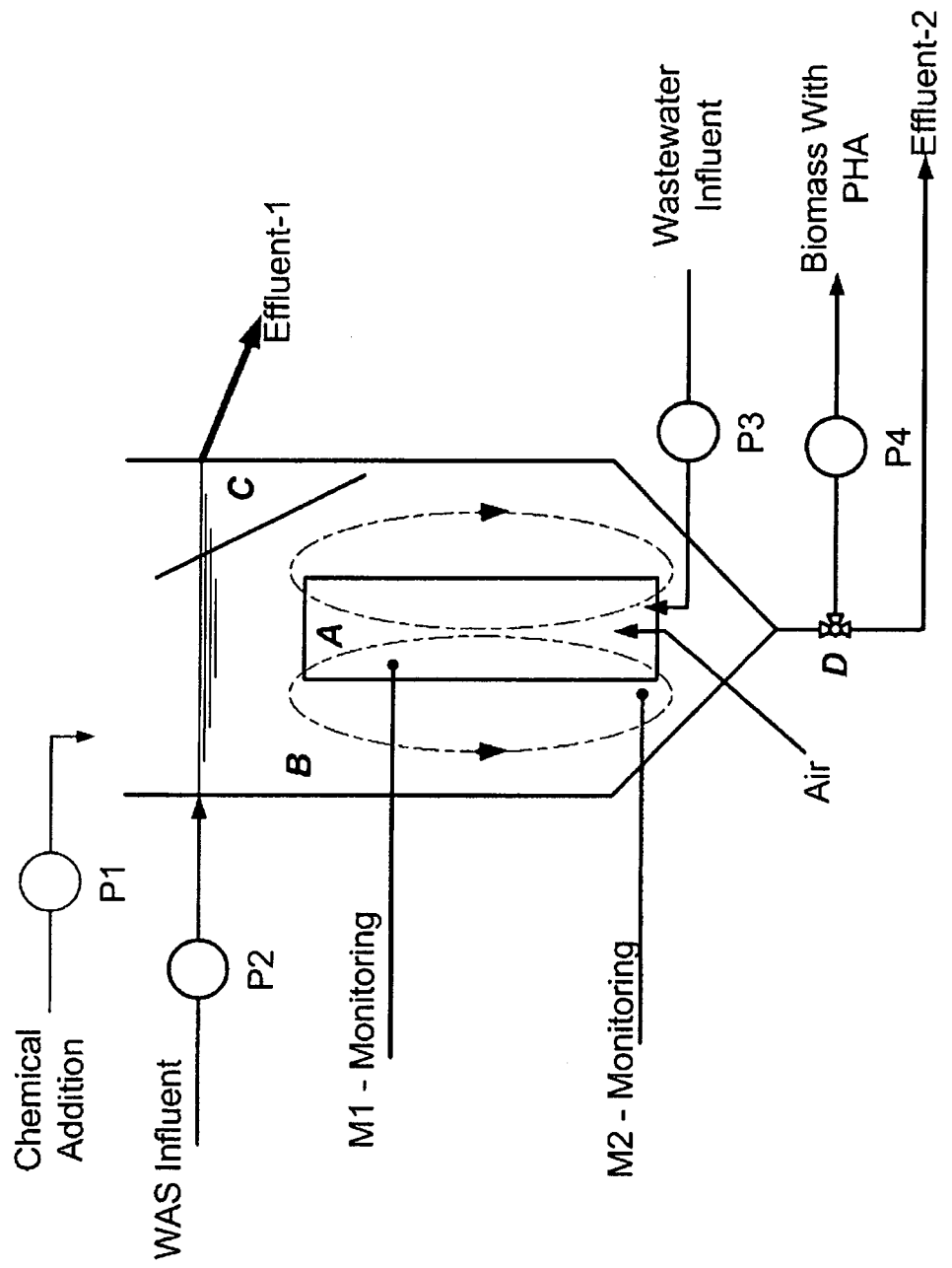
FIG. 11. Representative example of a constant volume aerobic PHA accumulation process.

The first example is a fed-batch PHA accumulation process wherein the active liquid (mixed liquor) volume increases over the course of the cycle (FIGS. 9 and 10). The second example is analogous except that a reactor configuration is shown where the active liquid volume is constant over the accumulation cycle (FIG. 11). The accumulation cycle is briefly described below.

Both examples include monitoring strategies for the assessment of the specific substrate consumption rate ($q_s$, Eqn. 2). For example, $q_s$ can be assessed by measurement of:
1. Biomass concentration, X based on UV/Vis spectroscopy.
2. Removal rates of RBCOD estimated from:
   a. UV/Vis spectroscopy and/or
   b. The interval of shift up and down trends of biomass respiration rates.

The mass or RBCOD fed to the process with each input of wastewater can be quantified. If only the RBCOD concentration is known, the mass fed into the process is equal to the volume fed times the RBCOD concentration.

According to Eqn. 1, the stimulating RBCOD concentration, s, for each fed-batch input must be greater than or equal to $s_m$. Methods for employing this concept can include the following steps:
1. Using a constant conservative fed-batch input to achieve theoretical PHA polymerization limiting kinetics. For example, an initial stimulation, s, of 200 mg-RBCOD/L is conservative based on currently available experimental data.
2. Estimating the extant $s_m$ based on the biomass response to each fed-batch input. Given the estimated $q_s$ to a fed-batch input stimulus of s, $s_m$ can be estimated due to an observed relationship between $s_m$ and $k_s$ (Eqn. 1). The relation can be calibrated specifically for different wastewater feeds as was performed for the results shown in FIG. 1.
3. Estimating the extant $s_m$ based on the biomass response to each fed-batch input by exploiting the anticipated relationship of Eqn. 1 using small but significant step-up and/or step-down shifts in s from one input to the next. A suitable optimization control algorithm can be applied to follow $s_m$ over the course of the accumulation cycle.

Example of a variable volume aerobic PHA accumulation process as shown in FIGS. 9 and 10. The system is shown at the start of the accumulation process before the first wastewater feed from P2. Just tank T2 is shown in FIG. 10. The system is shown at the end of the accumulation process (A) where the DAF feed is supplied (B) in order to separate the effluent from the concentrated biomass (C).

T1—an aerated constant volume tank used for rapidly combining wastewater influent (P2) with the recirculated mixed liquor (P3). This tank is a completely mixed stirred tank reactor that may be aerated.

T2—an aerated tank that can accommodate an increase of volume due to the wastewater influent added in T1. Here mixed liquor is recirculated back into reactor T2 from T1. This tank is an aerated completely mixed stirred tank reactor.

DAF—a reservoir for supplying dissolved air in order to achieve dissolved air flotation (DAF) in T2. The DAF concentrates the mixed liquor in reactor T2 after or near the end of the PHA accumulation process.

P5—a pump and valve assembly for the discharge of effluent and or thickened biomass after biomass separation by DAF.

P1—a means for chemical addition. Chemicals may be used for conditioning the biomass for reasons of improved DAF separation and/or for reasons of conditioning the biomass for improved PHA recovery after accumulation.

M1—on-line monitoring of water quality, biomass respiration, and biomass reflectivity in the constant volume tank T1.

M2—on-line monitoring of water quality, biomass respiration, biomass reflectivity; and liquid volume in the variable volume tank T2.

In one embodiment, the accumulation process proceeds as follows:

1. Waste activated sludge (WAS) of PAB-rich biomass from a wastewater treatment plant (WWTP) is fed into T2 with P4.
2. Mixing and aeration in T2 are turned off. No biomass is being recirculated (P3) such that all the WAS influent volume is held in T2.
3. The WAS is further concentrated by DAF and the underlying clarified effluent is discharged (P5). Thus the volume of mixed liquor in reactor T2 varies.
4. T2 and T1 aeration are started as is the recirculation pump P3. The initial conditions for the biomass concentration, dissolved organic matter concentration, and respiration rates are assessed based on monitoring from M1 and M2.
5. Fed batch dosing of wastewater influent is commenced (P2) such that:
   a. A targeted peak concentration is achieved in T1 in order to provide a sufficient accumulation stimulus for the biomass.
   b. The stimulus is sustained such that the biomass respiration rate is maintained at its extant maximum due to the selected pumping rates for P2 and P3 with on-line monitoring M1 and M2.
   c. Wastewater influent input and recirculation flow rates may be based on measured depletion of dissolved organic matter concentration, estimated depletion rates of dissolved organic matter concentration, and/or a shift down in respiration rates based on M1 and M2.
6. Wastewater input is continued until the available reactor volume of T2 has been used up, the target RBCOD mass has been fed, and/or the biomass exhibit signs of saturation in PHA due to, for example, a plateau or target in the trends of the biomass reflectivity.
7. At the end of the fed-batch process, aeration in T1 and T2 are turned off but mixing and recirculation in the two tanks can continue. At this time chemicals (P1) can be added in order to inhibit degradation of the stored PHA and to improve the DAF separation.
8. Biomass is concentrated in reactor T2 by DAF. Generally, after the PHA accumulation process has begun and reached a steady state condition, the volume of mixed liquor in reactor T1 is maintained at a generally constant level while the volume of mixed liquor in reactor T2 varies. Note also that reactor T1 in this embodiment is smaller than reactor T2 and consequently the volume of mixed liquor in reactor T1 is less than the volume of mixed liquor in reactor T2.
9. DAF-concentrated biomass and effluent are discharged from the process.
10. The reactor is ready for the next PHA-accumulation cycle.

Example of a constant volume aerobic PHA accumulation process as shown in FIG. 11.

A—an internal airlift providing rapid mixing of wastewater influent and the reactor mixed liquor in a localized zone of reduced volume. The airlift provides for aeration and mixing in the reactor. In this example the airlift is an internal open cylinder.

B—a downcomer which is in this illustration a concentric cylinder where the reactor contents are recirculated down back to the entrance of the airlift.

C—a quiescent zone in the reactor where airlift gas does not enter and where suspended solids entering this zone will settle and re-enter zone B.

M1—on-line monitoring of water quality, biomass respiration, and biomass reflectivity in the airlift.

M2—on-line monitoring of water quality, biomass respiration, biomass reflectivity, and liquid volume in the downcomer.

P1-P4. Pumps for control of WAS influent, wastewater influent, chemical addition, final effluent discharge (effluent-2), biomass harvesting.

An overflow (effluent-1) for discharging excess clarified liquid from the reactor so as to maintain constant total reactor liquid volume.

In this embodiment the accumulation process proceeds as follows:

1. The initially empty reactor is pumped full with WAS (P2).
2. Aeration is started. The initial conditions for the biomass concentration, dissolved organic matter concentration, and respiration rates are assessed based on monitoring from M1 and M2.
3. Fed batch dosing of wastewater influent is commenced (P3) such that:
   a. A targeted peak concentration is achieved in A in order to provide a sufficient accumulation stimulus for the biomass.
   b. The stimulus is sustained such that all the biomass has been exposed based on on-line monitoring M1 and M2, and/or the assessed internal recirculation rate.
   c. Subsequent fed-batch wastewater influent inputs can be based on measured depletion of dissolved organic matter concentration, estimated depletion rates of dissolved organic matter concentration, and/or a shift down in respiration activity based on M1 and M2.
4. Wastewater input is continued until the target RBCOD mass has been fed, and/or the biomass exhibit signs of saturation in PHA due to, for example, a plateau in the trends of the biomass reflectivity.

5. At the end of the fed-batch process aeration may briefly continue to maintain mixing while chemicals are added (P1). Chemicals may be added in order to inhibit degradation of the stored PHA and to improve biomass separation by gravity settling.
6. Biomass is concentrated in the reactor by gravity settling.
7. Concentrated biomass and effluent are discharged from the process (D and P4).
8. The reactor is ready for the next PHA-accumulation cycle.

What is claimed is:

1. A fed-batch method for producing high molecular weight polyhydroxyalkanoates (PHAs) in biomass, comprising:
    directing biomass into a reactor having at least one stimulating zone and at least one maintenance zone wherein the stimulating zone and maintenance zone are at least partially separated by a physical structure;
    intermittently and repeatedly stimulating the biomass respiration rate of the biomass during a PHA accumulation process by exposing at least a fraction of the biomass to an elevated substrate concentration in the at least one stimulating zone while at least a portion of the remaining biomass is exposed to substrate concentrations in the maintenance zone that are less than the average substrate concentrations in the stimulating zone;
    monitoring and assessing, at least indirectly, the respiration rate of the biomass in the maintenance zone where the substrate concentration therein is on average less than the substrate concentration in the stimulating zone;
    circulating the biomass back and forth between the stimulating zone and the maintenance zone;
    controlling the frequency of biomass recirculation or rate of substrate addition such that the respiration rate of the biomass in the maintenance zone does not decrease by more than 70% of the extant achievable maximum respiration rate of the biomass;
    retaining the biomass in the reactor until a significant level of PHA is accumulated by the biomass;
    harvesting PHA rich biomass from the reactor;
    wherein repeated exposure of the biomass to elevated substrate concentrations is achieved by directing substrate into the stimulating zones and mixing the substrate with recirculated biomass;
    wherein the elevated concentrations of the substrate used to repeatedly stimulate the biomass respiration rate between 10 and 1000 mg-Chemical Oxygen Demand (COD)/L;
    wherein the above combination of method steps provides for PHA accumulation and wherein the accumulated PHA, when separated from the biomass, includes an average molecular weight of at least 400,000 g/mole.

2. The method of claim 1 including assessing the biomass respiration rate in the maintenance zone with monitoring methods such as UV/VIS spectroscopy, conductivity, ion electrodes, other chemical sensors, or combinations thereof.

3. The method of claim 1 wherein the substrate and biomass are mixed together to form a substrate and biomass mixture with elevated substrate concentration, and the method includes controlling the frequency that any given biomass fraction is subject to stimulation by elevated substrate concentration as a function of the concentration of dissolved organic carbon or the concentration of dissolved COD in the maintenance zone.

4. The method of claim 1 wherein the substrate and biomass are mixed together to form a substrate and biomass mixture with elevated stimulating substrate concentration, and the method further includes controlling the frequency that the biomass or fractions thereof are subject to stimulation by elevated substrate concentration based on the biomass respiration derived from monitoring dissolved oxygen and or carbon dioxide concentrations.

5. The method according to claim 1 wherein the reactor comprises a batch reactor and at least one separate tank and wherein the biomass is directed into the batch reactor and is contained within mixed liquor in the batch reactor, and the method includes directing the mixed liquor from the batch reactor to the at least one separate tank and feeding the substrate to the biomass in the separate tank, and wherein the separate tank includes a volume of mixed liquor less than the volume of mixed liquor in the batch reactor, and wherein the average concentration of the substrate in the separate tank is higher than the average concentration of the substrate in the batch reactor.

6. The method according to claim 1 including concentrating the biomass in a reactor before, during, or after PHA accumulation in the biomass.

7. The method of claim 1 wherein controlling the frequency that the biomass or fractions thereof are subject to stimulation by the elevated substrate concentration includes:
    (i) intermittently pumping the substrate into the reactor that includes the biomass,
    (ii) circulating biomass from the maintenance zone having a relatively low average concentration of substrate to the stimulating zone having a relatively high average concentration of substrate.

8. The method of claim 1 wherein the biomass is contained within mixed liquor and the substrate is fed intermittently to the biomass in the stimulating zone; and wherein the frequency of feeding the substrate to the biomass is controlled by sensing the dissolved oxygen concentration in the mixed liquor and feeding substrate to the biomass in response to an increase in dissolved oxygen concentration in the mixed liquor, over a selected time, that is greater than a selected threshold value.

9. The method of claim 8 including controlling the frequency of feeding the substrate to the biomass by correlating the dissolved oxygen concentration in the mixed liquor with biomass respiration rate, and feeding of the substrate to the biomass in response to a decrease in respiration rate, over the selected time, that is less than a selected threshold value.

10. The method of claim 1 including treating a wastewater stream and producing a mixed cultured biomass and harvesting the mixed cultured biomass and feeding the mixed cultured biomass to the reactor; and
    wherein the method entails utilizing at least a portion of the wastewater stream or an alternative wastewater stream as a source for the substrate fed to the mixed cultured biomass.

11. A fed-batch method for producing high molecular weight polyhydroyxalkanoates (PHAs) in biomass, comprising:
    directing mixed liquor containing biomass into a reactor including at least one biomass stimulating zone and at least one biomass maintenance zone wherein the stimulating zone and the maintenance zone are at least partially separated by a physical structure;
    directing substrate into the stimulating zone;
    intermittently and repeatedly stimulating the biomass respiration rate during a PHA accumulation process for at least a fraction of the biomass in the reactor by exposing the fraction of the biomass to an elevated substrate concentration in the stimulating zone;
    after exposing the fraction of the biomass to the elevated substrate concentration in the stimulating zone, transferring at least a portion of the fraction of biomass from the stimulating zone to the maintenance zone where the substrate concentration is less than the elevated substrate concentration in the stimulating zone;

monitoring and assessing, at least indirectly, the respiration rate of the biomass within the maintenance zone;

maintaining the respiration rate of the biomass within the maintenance zone such that the respiration rate does not decrease by more than 70% of the extant achievable maximum respiration rate of the biomass by controlling the frequency that the biomass is repeatedly subjected to the elevated substrate concentration in the stimulating zone;

circulating the mixed liquor containing biomass back and forth between the stimulating zone and the maintenance zone such that fractions of biomass are repeatedly exposed to the elevated substrate concentration in the stimulating zone and wherein the fractions of biomass are repeatedly exposed to a lower substrate concentration in the maintenance zone;

wherein the elevated substrate concentration in the stimulating zone is between 10 and 1,000 mg-COO/L; and wherein the above combination of steps produces PHA and wherein the produced PHA includes an average molecular weight of at least 400,000 g/mole.

12. The method of claim 1 wherein the reactor includes a first tank that includes the stimulating zone and a second tank that includes the maintenance zone; and wherein the biomass is contained within mixed liquor and the method includes circulating the mixed liquor and biomass between the first and second tanks and repeatedly subjecting the biomass to elevated substrate concentrations in the first tank while the biomass in the second tank is subjected to substrate concentrations less than the substrate concentrations in the first tank.

13. The method of claim 1 wherein the stimulating zone and maintenance zone are included in a single tank, and wherein the method includes circulating the biomass between the stimulating zone and the maintenance zone in the signal tank such that the biomass is repeatedly subjected to elevated substrate concentrations in the stimulating zone.

14. The method of claim 1 wherein the elevated substrate concentrations in the stimulating zone is between 20 and 500 mg.COD/L.

15. The method of claim 11 wherein intermittently and repeatedly stimulating the biomass respiration rate includes interrupting the supply of substrate to at least fractions of the biomass a plurality of times, and controlling the frequency of substrate supply such that the respiration rate of the biomass does not decrease by more than 70% of the extant achievable maximum respiration rate of the biomass.

16. The method of claim 11 wherein the reactor includes a first tank that includes the stimulating zone and the second tank that includes the maintenance zone; and wherein the method includes circulating the mixed liquor and biomass between the first and second tanks and repeatedly subjecting the biomass to the elevated substrate concentration in the first tank while the biomass in the second tank is subjected to a substrate concentration less than the substrate concentration in the first tank.

17. The method of claim 11 wherein the stimulating zone and the maintenance zone are included in a single tank and wherein the method includes circulating the mixed liquor and biomass back and forth between the stimulating zone and the maintenance zone in the single tank.

18. The method of claim 11 wherein the fed-batch method of producing high molecular weight PHAs in biomass comprises:

directing waste activated sludge resulting from a wastewater treatment process to the reactor and wherein the waste activated sludge includes PHA-accumulating biomass;

circulating the biomass from the maintenance zone to the stimulating zone and continuing to recirculate the biomass between the maintenance zone and the stimulating zone;

feeding an organic carbon-containing substrate to the PHA-accumulating biomass in the stimulating zone by intermittently or continuously supplying the substrate to the stimulating zone over a period of time; and wherein the respiration rate of the biomass is stimulated and maintained during the PHA accumulation process by exposing biomass in the stimulating zone to the elevated substrate concentration while the substrate concentration in the maintenance zone is less than the elevated substrate concentration in the stimulating zone.

* * * * *